United States Patent

Kato et al.

[11] Patent Number: 5,989,452
[45] Date of Patent: Nov. 23, 1999

[54] FLUOROALKENYL DERIVATIVE AND LIQUID CRYSTAL COMPOSITION

[75] Inventors: Takashi Kato; Shuichi Matsui; Kazutoshi Miyazawa; Norihisa Hachiya; Etsuo Nakagawa, all of Chiba, Japan

[73] Assignee: Chisso Corporation, Osaka, Japan

[21] Appl. No.: 09/051,353

[22] PCT Filed: Oct. 11, 1996

[86] PCT No.: PCT/JP96/02950

§ 371 Date: Apr. 8, 1998

§ 102(e) Date: Apr. 8, 1998

[87] PCT Pub. No.: WO97/13738

PCT Pub. Date: Apr. 17, 1997

[30] Foreign Application Priority Data

Oct. 12, 1995 [JP] Japan .................................. 7-292095

[51] Int. Cl.[6] .......................... C09K 19/30; C09K 19/12; C09K 19/34; C07C 19/08
[52] U.S. Cl. ............................. 252/299.63; 252/299.66; 252/299.61; 570/128; 570/129
[58] Field of Search ......................... 252/299.63, 299.66, 252/299.61; 570/128, 129

[56] References Cited

U.S. PATENT DOCUMENTS 5,183,587 2/1993 Kitano et al. ....................... 252/299.63
5,653,911 8/1997 Kondo et al. ....................... 252/299.01

FOREIGN PATENT DOCUMENTS 0168683 1/1986 European Pat. Off. .
0679707 11/1995 European Pat. Off. .
61-83136 4/1986 Japan .
63-142091 6/1988 Japan .
4-30382 5/1992 Japan .
WO93/07234 4/1993 WIPO .

Primary Examiner—C. H. Kelly
Attorney, Agent, or Firm—Wenderoth, Lind & Ponack L.L.P.

[57] ABSTRACT

The present invention is to provide liquid crystalline compounds having a wide temperature range of a liquid crystal phase, low viscosity, and large ratio of elastic constants; liquid crystal compositions comprising the compound; and liquid crystal display devices comprising the composition; the liquid crystalline compounds being fluoroalkenyl derivatives expressed by the general formula (1)

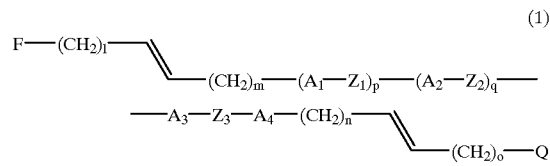

wherein $A_1$, $A_2$, $A_3$, and $A_4$ independently represent trans-1,4-cyclohexylene group or 1,4-phenylene group; $Z_1$, $Z_2$, and $Z_3$ independently represent —$(CH_2)_2$—, —CH=CH—, —C≡C—, or a single bond; Q represents H or F; l is an integer of 1 to 5; m, n, and o are independently an integer of 0 to 5; p and q are independently an integer of 0 or 1; and each element which constitutes the derivatives may be an isotope of the element.

13 Claims, 1 Drawing Sheet

FLUOROALKENYL DERIVATIVE AND LIQUID CRYSTAL COMPOSITION

This application is a 371 application of International Application No. PCT/JP96/02950 filed Oct. 11, 1996.

TECHNICAL FIELD

The present invention relates to liquid crystalline compounds and liquid crystal compositions. More specifically, it relates to novel liquid crystalline compounds having a fluorine substituted alkenyl group at an end and having a fluorine substituted or unsubstituted alkenyl group at the other end of the molecule; relates to liquid crystal compositions comprising the compound; and relates to liquid crystal display devices comprising the composition.

BACKGROUND ART

Display devices comprising liquid crystalline compounds have widely been employed for the displays of watches, tabletop calculators, word processors, TV sets, or the likes. These display devices employ the optical anisotropy and dielectric anisotropy of liquid crystalline compounds.

Liquid crystal phase exists between a solid phase and a liquid phase, and the liquid crystal phase includes a nematic phase, smectic phase, and cholesteric phase as its specific form. Among which, the nematic phase is most in use at present for display devices. As the specific type of display mode, TN (twisted nematic) mode, DS (dynamic scattering) mode, GH (guest-host) mode, DAP (deformation of aligned phases) mode all of which exhibit electro-optic effects have been developed. Meanwhile, display of liquid crystals in color is further progressing lately, and particularly devices of TFT (thin-film-transistor) mode and STN (super twisted nematic) mode both of which form a class of TN mode have now become a main current.

Whereas many liquid crystalline compounds including ones which are currently at a stage of research are known up to now, compounds which can be filled in display devices as a single compound to actually use as liquid crystal composition have not been developed. This is because whereas liquid crystalline compounds expected to be used as a material for display devices must exhibit a liquid crystal phase at room temperature, at which display devices are most often used, as well as in a temperature range as wide as possible with the room temperature being its center; must be sufficiently stable against environmental factors under conditions in which the devices are used; and must have physical properties sufficient to drive display devices, no compounds which can satisfy these requirements by a single compound have been found. Accordingly, it is an actual circumstance at present that several kind or several tens kind of liquid crystalline compounds, and non liquid-crystalline compounds when necessary, are mixed to prepare liquid crystal compositions having the required characteristics. It is considered to be necessary that these liquid crystal compositions are stable against moisture, light, heat, and air which are usually present under the conditions in which display devices are used; are stable also against electric field and electromagnetic radiation; and are chemically stable against liquid crystalline compounds to be mixed. Also, it is considered to be necessary that liquid crystal compositions have an appropriate value of physical properties such as optical anisotropy ($\Delta n$), dielectric anisotropy ($\Delta \epsilon$), viscosity ($\eta$), electroconductivity, and ratio of elastic constants ($K_{33}/K_{11}$; $K_{33}$: bend elastic constant, $K_{11}$: splay elastic constant) depending on the display modes and the shape of display devices. Further, it is important that each component in liquid crystal compositions have a good mutual solubility to one another.

It is considered to be necessary that the liquid crystal compounds used in displays of STN mode particularly have a low viscosity, large $K_{33}/K_{11}$, and wide temperature range of a liquid crystal phase in addition to the properties described above. Further, a low threshold voltage (Vth) is quite recently considered to be necessary accompanied with driving of display devices at a low voltage.

That is, low viscosity is an essential property for achieving a high speed response. Also, large $K_{33}/K_{11}$ makes the change of transmittance around $V_{th}$ steep and makes the production of display devices of a high contrast possible. As the compounds exhibiting a large $K_{33}/K_{11}$, ones having an alkenyl group as a lateral chain, for example, compounds expressed by the formula (a) disclosed in Japanese patent publication No. Hei 4-30382 and compounds expressed by the formula (b) disclosed in Japanese patent publication No. Hei 7-2653 are already known. However, since these compounds have a strong tendency to develop a smectic phase by themselves, they sometimes separate crystals or develop a smectic phase particularly at low temperatures when used as a component of liquid crystal compositions. Thus, the compounds can not be said to be good in mutual solubility at low temperatures.

Besides, whereas these compounds exhibit some extent of viscosity reducing effect on liquid crystal compositions to which the compounds are mixed, the compounds have a defect of lowering clearing point, and have a problem that they remarkably lower $\Delta \epsilon$ when added to liquid crystal compositions having a high $\Delta \epsilon$ used for the purpose of driving the devices at low voltages, since the compounds themselves have a remarkably low $\Delta \epsilon$.

As compounds having a structure similar to that of the compounds of the present invention, ones expressed by the formula (c) are known as shown in U.S. Pat. No. 5,183,587. However, these compounds have a problem that heat stability is very poor.

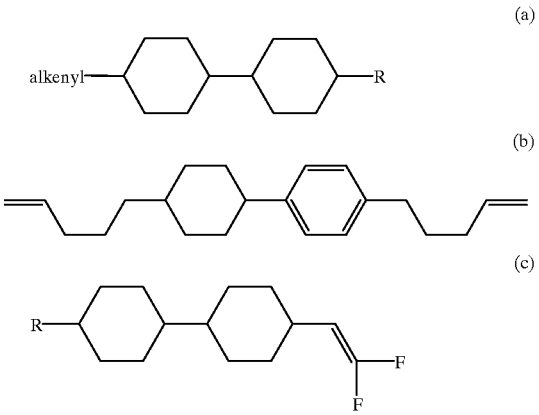

In addition, compounds having only an alkenyl group or a halogen substituted alkenyl group as a terminal group in the molecule are disclosed, for example, in Laid-open Japanese Patent Publication Nos. Sho 61-83136 and Sho 63-142091. However, these compounds are insufficient for collectively achieving the effect of maintaining or raising clearing point and the effect of not lowering $\Delta \epsilon$ (not raising $V_{th}$) of liquid crystal compositions. Besides, these compounds have a defect in solubility to other known liquid crystal compounds, particularly in that at low temperatures.

From such circumstances in conventional technology, development of liquid crystalline compounds having a low viscosity, large $K_{33}/K_{11}$, excellent heat stability, wide temperature range of a liquid crystal phase, comparatively low $V_{th}$, and improved solubility at low temperatures has been desired.

DISCLOSURE OF THE INVENTION

An object of the present invention is to solve the defects in conventional technology described above. Another object of the present invention is to provide liquid crystalline compounds having a low viscosity, large $K_{33}/K_{11}$, excellent heat stability, wide temperature range of a liquid crystal phase, and improved solubility at low temperatures in particular; to provide liquid crystal compositions comprising the compound; and to provide liquid crystal display devices comprising the composition.

The present invention for achieving the objects described are summarized as follows:

(1) A fluoroalkenyl derivative expressed by the general formula (1)

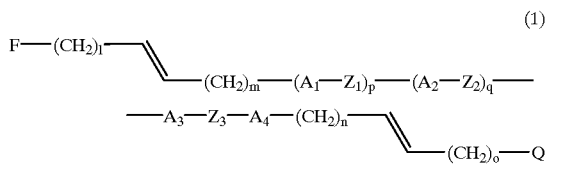

wherein $A_1$, $A_2$, $A_3$, and $A_4$ independently represent trans-1,4-cyclohexylene group or 1,4-phenylene group at least one hydrogen atom of which six-membered ring may be replaced by a halogen atom; $Z_1$, $Z_2$, and $Z_3$ independently represent $-(CH_2)_2-$, $-CH=CH-$, $-C\equiv C-$, or a single bond; Q represents H or F; l is an integer of 1 to 5; m, n, and o are independently an integer of 0 to 5; p and q are independently an integer of 0 or 1; and each element which constitutes the derivative may be an isotope of the element.

(2) The fluoroalkenyl derivative recited in paragraph (1) above wherein $Z_3$ represents a single bond; both $A_3$ and $A_4$ represent trans-1,4-cyclohexylene group; and both p and q are 0.

(3) The fluoroalkenyl derivative recited in paragraph (1) above wherein both $Z_2$ and $Z_3$ represent a single bond; $A_2$, $A_3$, and $A_4$ represent trans-1,4-cyclohexylene group; p is 0; and q is 1.

(4) The fluoroalkenyl derivative recited in paragraph (1) above wherein both $Z_2$ and $Z_3$ represent a single bond; both $A_2$ and $A_4$ represent trans-1,4-cyclohexylene group; $A_3$ represents 1,4-phenylene group; p is 0; and q is 1.

(5) The fluoroalkenyl derivative recited in paragraph (1) above wherein $Z_1$, $Z_2$, and $Z_3$ represent a single bond; both $A_1$ and $A_4$ represent trans-1,4-cyclohexylene group; both $A_2$ and $A_3$ represent 1,4-phenylene group; and both p and q are 1.

(6) A liquid crystal composition comprising at least 2 components and comprising at least one fluoroalkenyl derivative recited in any one of paragraphs (1) to (5) above.

(7) A liquid crystal composition comprising, as a first component, at least one fluoroalkenyl derivative recited in any one of paragraphs (1) to (5) above, and comprising, as a second component, at least one compound selected from the group consisting of the compounds expressed by any one of the general formulas (2), (3), and (4)

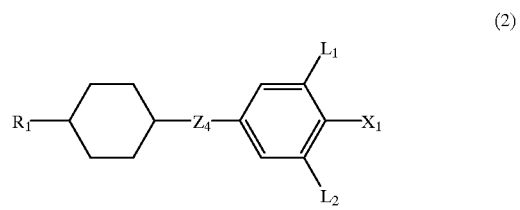

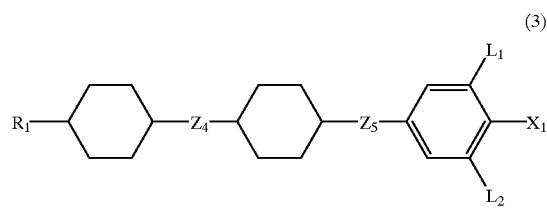

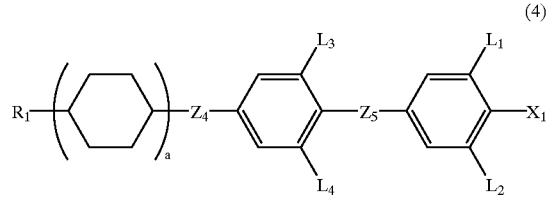

wherein $R_1$ represents an alkyl group having 1 to 10 carbon atoms; $X_1$ represents F, Cl, $OCF_3$, $OCF_2H$, $CF_3$, $CF_2H$, or $CFH_2$; $L_1$, $L_2$, $L_3$, and $L_4$ independently represent H or F; $Z_4$ and $Z_5$ independently represent $-(CH_2)_2-$, $-CH=CH-$, or a single bond; and a is 1 or 2.

(8) A liquid crystal composition comprising, as a first component, at least one fluoroalkenyl derivative recited in any one of paragraphs (1) to (5) above, and comprising, as a second component, at least one compound selected from the group consisting of the compounds expressed by any one of the general formulas (5), (6), (7), (8), and (9)

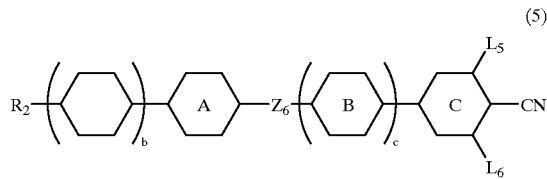

wherein $R_2$ represents F, an alkyl group having 1 to 10 carbon atoms, or an alkenyl group having 2 to 10 carbon atoms, in which alkyl group or alkenyl group one or more non-adjacent methylene groups ($-CH_2-$) may each be replaced by an oxygen atom ($-O-$); ring A represents trans-1,4-cyclohexylene group, 1,4-phenylene group, pyrimidine-2,5-diyl group, or 1,3-dioxane-2,5-diyl group; ring B represents trans-1,4-cyclohexylene group, 1,4-phenylene group, or pyrimidine-2,5-diyl group; ring C represents trans-1,4-cyclohexylene group or 1,4-phenylene group; $Z_6$ represents $-(CH_2)_2-$, $-COO-$, or a single bond; $L_5$ and $L_6$ independently represent H or F; and b and c are independently 0 or 1, (6)

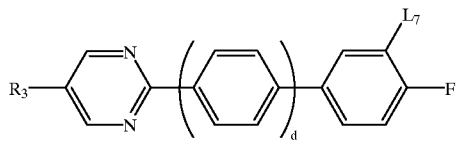

wherein $R_3$ represents an alkyl group having 1 to 10 carbon atoms; $L_7$ represents H or F; and d is 0 or 1, (7)

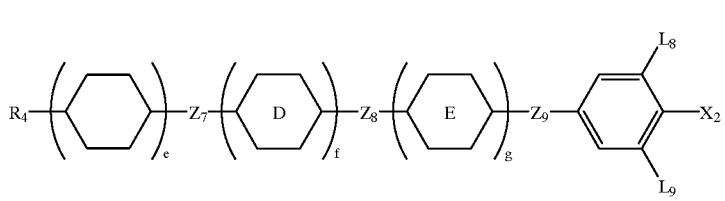

wherein $R_4$ represents an alkyl group having 1 to 10 carbon atoms; ring D and ring E independently represent trans-1,4-cyclohexylene group or 1,4-phenylene group; $Z_7$ and $Z_8$ independently represent —COO— or a single bond; $Z_9$ represents —COO— or —C≡C—; $L_8$ and $L_9$ independently represent H or F; $X_2$ represents F, $OCF_3$, $OCF_2H$, $CF_3$, $CF_2H$, or $CFH_2$; and e, f, and g are independently 0 or 1, (8)

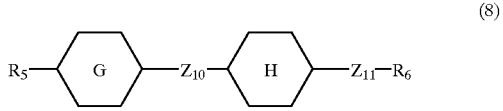

wherein $R_5$ and $R_6$ independently represent an alkyl group having 1 to 10 carbon atoms or an alkenyl group having 2 to 10 carbon atoms, in which alkyl or alkenyl group one or more non-adjacent methylene groups (—$CH_2$—) may each be replaced by an oxygen atom (—O—); ring G represents trans-1,4-cyclohexylene group, 1,4-phenylene group, or pyrimidine-2,5-diyl group; ring H represents trans-1,4-cyclohexylene group or 1,4-phenylene group; $Z_{10}$ represents —C≡C—, —COO—, —($CH_2$)$_2$—, —CH=CH—C≡C—, or a single bond; and $Z_{11}$ represents —COO— or a covalent bond, cyclohexylene group or 1,4-phenylene group ; $Z_{12}$ and $Z_{14}$ independently represent —COO—, —($CH_2$)$_2$—, or a single bond; $Z_{13}$ represents —CH=CH—, —C≡C—, —COO—, or a single bond; and h is 0 or 1.

(9) A liquid crystal composition comprising, as a first component, at least one fluoroalkenyl derivative recited in any one of paragraphs (1) to (5) above, comprising, as a part of a second component, at least one compound selected from the group consisting of the compounds expressed by any one of the general formulas (2), (3), and (4); and comprising, as other part of the second component, at least one compound selected from the group consisting of the compounds expressed by any one of the general formulas (5), (6), (7), (8), and (9).

(10) A liquid crystal display device comprising a liquid crystal composition recited in any one of paragraphs (6) to (9) above.

BEST MODE FOR CARRYING OUT THE INVENTION

Figure 1:
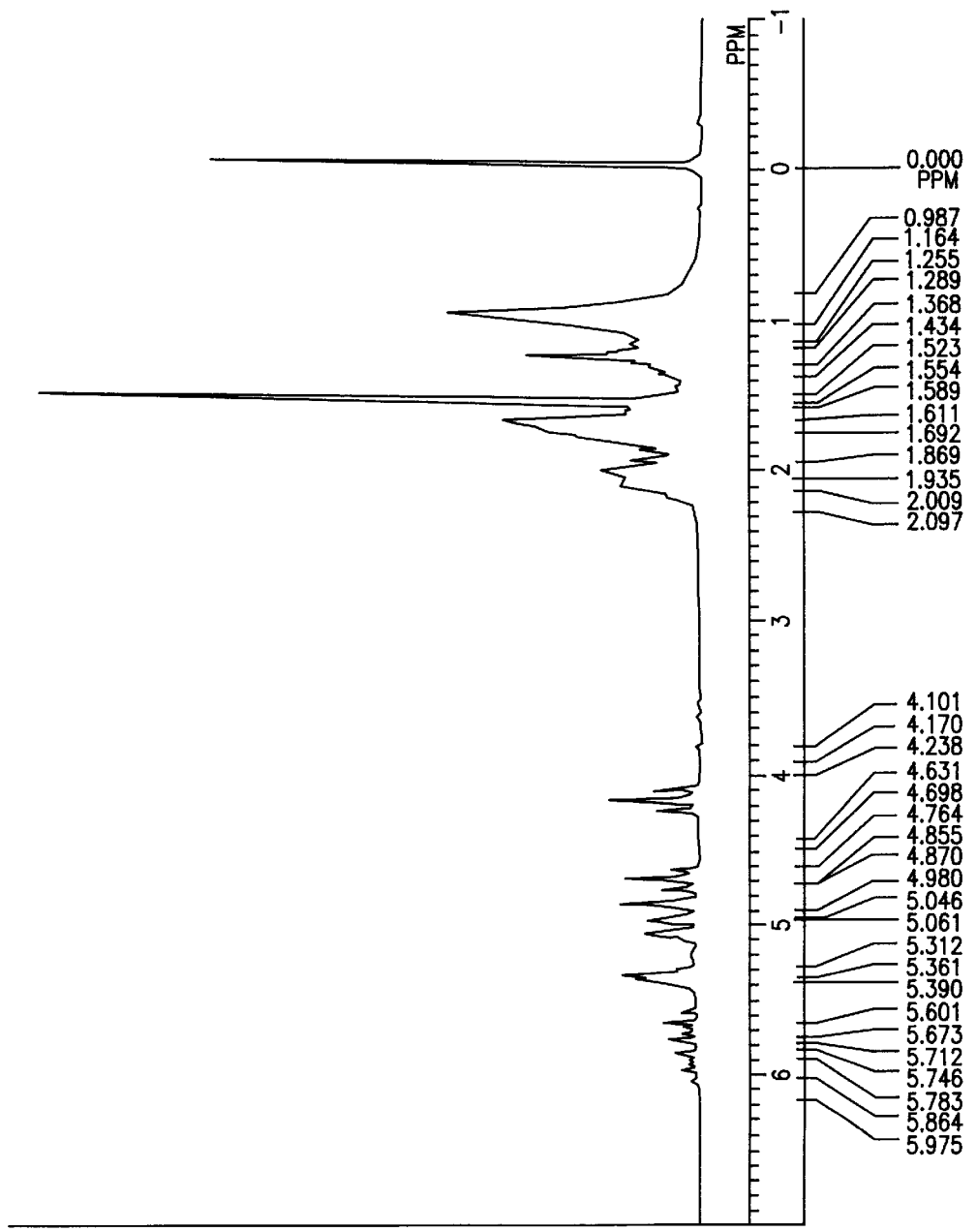
FIG. 1 is a chart showing a nuclear magnetic resonance spectrum indicating the structure of a compound of the present invention.

Compounds of the present invention expressed by the general formula (1) are ones of two- to four-ring system compounds and are principally characterized by having a specific structure formed by introducing an alkenyl group replaced by fluorine atom in one end and also introducing an alkenyl group in the other end of the molecule.

While these compounds of the present invention are applied as a component of liquid crystal compositions for display devices, the compounds are extremely stable physically and chemically under conditions in which the display devices are used. Besides, the compounds have a good (9)

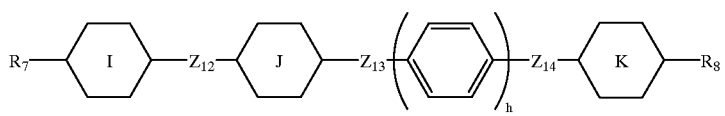

wherein $R_7$ and $R_8$ independently represent an alkyl group having 1 to 10 carbon atoms or an alkenyl group having 2 to 10 carbon atoms, in which alkyl or alkenyl group one or more non-adjacent methylene groups (—$CH_2$—) may each be replaced by an oxygen atom (—O—) ring I represents trans-1,4-cyclohexylene group, 1,4-phenylene group, or pyrimidine-2,5-diyl group; ring J represents trans-1,4-cyclohexylene group, 1,4-phenylene group at least one hydrogen atom on which ring may be replaced by F, or pyrimidine-2,5-diyl group; ring K represents trans-1,4- solubility in liquid crystal compositions even at low temperatures and exhibit a wide temperature range of a nematic phase, low viscosity, medium degree of Δε, and large $K_{33}/K_{11}$. Further, it is possible to optionally adjust desired physical properties by properly selecting a ring structure, bonding group, and structure of a lateral chain from the molecule constituting elements.

Accordingly, properties of liquid crystal compositions can be improved as described in 1) to 4) below by using the compound of the present invention. Thus, it is possible to provide liquid crystal display devices which are stable against external environment and which further make a high speed response, high contrast, and driving at a low voltage possible, by improving the properties of liquid crystal compositions. Particularly for TFT mode, liquid crystal display devices improved even in the steepness and viewing angle can be provided through the improvement of the properties of the compositions.

1) Viscosity can be reduced while maintaining or raising clearing point.
2) $\Delta\epsilon$ is maintained and $V_{th}$ is kept from raising.
3) Stabilized nematic liquid crystal compositions which do not separate crystals or do not develop a smectic phase even at extremely low temperatures can be produced.
4) $K_{33}/K_{11}$ can be increased.

Excellent properties of the compounds of the present invention described above are considered to be caused by a synergistic effect of a fluorine substituted or unsubstituted alkenyl group at one end and an alkenyl group always substituted by fluorine atom at the other end of the molecule.

While any compounds of the present invention expressed by the general formula (1) exhibit preferable properties as described above, they can be made to a component for liquid crystal compositions complied with their purposes by selecting a proper group or numeral for $A_1$, $A_2$, $A_3$, $A_4$, $Z_1$ $Z_2$, $Z_3$, l, m, n, o, p, and q in the general formula (1).

For instance, particularly for producing liquid crystal compositions of which the temperature of developing a liquid crystal phase desirably shifts to higher temperature side, it is sufficient to select compounds of four-ring system wherein p and q are 1, and for other end uses, it is sufficient to select compounds of two- or three-ring system. Also, for liquid crystal compositions desirably having a high $\Delta\epsilon$, it is sufficient to use compounds in which one or two fluorine atoms are substituted for hydrogen atoms on 1,4-phenylene group in the molecule so that their dipole moment faces the same direction as that of the dipole moment of the alkenyl group in which a fluorine atom is substituted, and such compositions exhibit even excellent solubility at low temperatures.

Improvement in optical anisotropy ($\Delta n$) can be adjusted by selecting a proper group and numeral for the $A_1$, $A_2$, $A_3$, $A_4$, $Z_1$, $Z_2$, $Z_3$, p, and q. For instance, for producing liquid crystal compositions desirably having a high $\Delta n$, it is sufficient to use a compound having many 1,4-phenylene groups and having single bond as each of $Z_1$, $Z_2$, and $Z_3$. Conversely for liquid crystal compositions desirably having a small $\Delta n$, it is sufficient to use a compound having many trans-1,4-cyclohexylene groups.

Now, assuming that $R_9$ represents groups expressed by the following formula (d), $R_{10}$ represents groups expressed by the following formula (e),

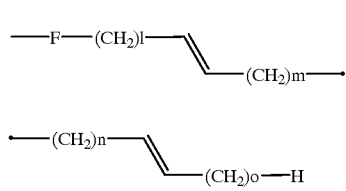

Cyc represents trans-1,4-cyclohexylene group, Phe represents 1,4-phenylene group at least one hydrogen atom on the six-membered ring may be replaced by a halogen atom, the compounds of the present invention expressed by the general formula (1) can be classified as follows:

Compounds having two six-membered rings:

 (1a)

 (1b)

Compounds having three six-membered rings:

 (1c)

 (1d)

 (1e)

 (1f)

Compounds having four six-membered rings:

 (1g)

 (1h)

 (1i)

 (1j)

 (1k)

 (1l)

 (1m)

 (1n)

Among these compounds, compounds expressed particularly by the formula (1a), (1c), or (1g) are preferable for achieving the objects of the present invention.

Compounds expressed by the formula (1a) can further be developed into the compounds expressed by the following formula (1aa) or (1ab):

 (1aa)

 (1ab)

Among these compounds, compounds expressed by the formula (1aa) are especially preferable. Since these two-ring system compounds are remarkably low in viscosity while having a comparatively high clearing point, and exhibit a medium degree of $\Delta\epsilon$ and large $K_{33}/K_{11}$, it is possible to considerably reduce only the viscosity of liquid crystal compositions without lowering their clearing point when such compounds are used as a component of the compositions.

Compounds expressed by the formula (1c) can further be developed into the compounds expressed by the following formulas (1ca) to (1cc):

 (1ca)

 (1cb)

 (1cc)

Among these compounds, the compounds expressed by the formula (1ca) or (1cb) are especially preferable. These three-ring system compounds also exhibit properties similar to those of the two-ring system compounds described above, and clearing point of liquid crystal compositions can further be raised by using such compounds as a component of the compositions.

Also, compounds expressed by the formula (1g) can further be developed into the compounds expressed by one of the following formulas (1ga) to (1gc):

(1ga)

(1gb)

(1gc)

Among these compounds, the compounds expressed by the formula (1gb) or (1gc) are especially preferable. Since these four-ring system compounds are also comparatively low in viscosity while having a high clearing point, it is possible to raise only clearing point of liquid crystal compositions while maintaining their viscosity by using such compounds as a component of the compositions.

While compounds expressed by the formula (1aa), (1ca), (1cb), (1gb), or (1gc) can be said to be preferable examples as described above, compounds expressed by one of the following formulas (1-1) to (1-4) can be mentioned as more preferable ones among such compounds as mentioned just above.

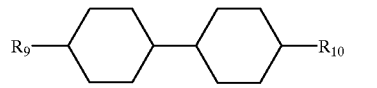
(1-1)

(1-2)

(1-3)

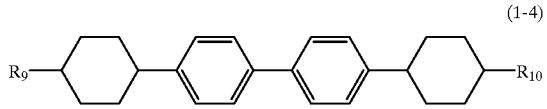
(1-4)

While $R_9$ in all compounds described above is an alkenyl group having 3 to 12 carbon atoms wherein one hydrogen atom at ω-position is replaced by fluorine atom, particularly preferable groups among them are 3-fluoro-1-propenyl, 4-fluoro-1-butenyl, 5-fluoro-pentenyl, 6-fluoro-3-hexenyl, and 7-fluoro-3-heptenyl. While $R_{10}$ is an alkenyl group having 2 to 12 carbon atoms, particularly preferable groups among them are ethenyl, 1-propenyl, 3-butenyl, and 3-pentenyl.

While the liquid crystal compositions provided by the present invention may comprise only a first component comprising at least one fluoroalkenyl derivative of liquid crystalline compound expressed by the general formula (1), the compositions preferably comprise, as a second component, at least one compound selected from the group consisting of the compounds expressed by any one of the general formulas (2), (3), and (4) (hereinafter referred to as second A component) and/or at least one compound selected from the group consisting of the compounds expressed by any one of the general formulas (5), (6), (7), (8), and (9) (hereinafter referred to as second B component) in addition to the first component. Further, one or more known compounds may be mixed to the liquid crystal compositions of the present invention as a third component for the purpose of adjusting $V_{th}$, temperature range of a liquid crystal phase, Δn, Δε, and viscosity.

As preferable examples of the compounds included in the general formula (2), (3), or (4) among the second A component, compounds expressed by one of the formulas (2-1) to (2-15), (3-1) to (3-48), and (4-1) to (4-55) can be mentioned, respectively.

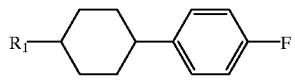
(2-1)

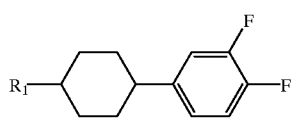
(2-2)

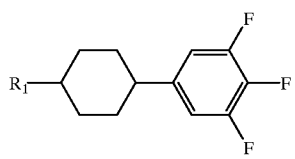
(2-3)

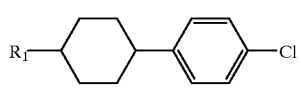
(2-4)

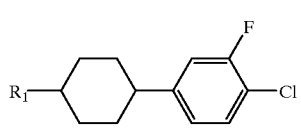
(2-5)

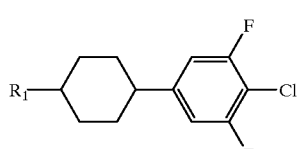
(2-6)

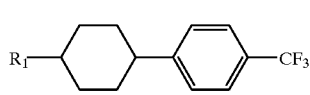
(2-7)

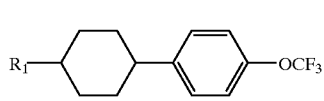
(2-8)

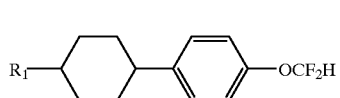
(2-9)

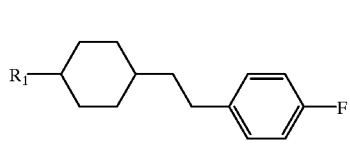
(2-10)

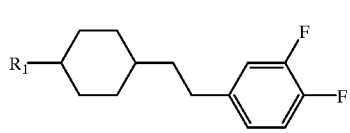
(2-11)

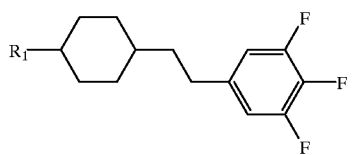 (2-12)
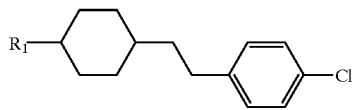 (2-13)
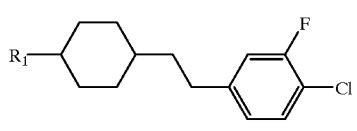 (2-14)
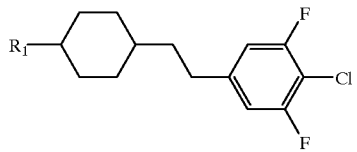 (2-15)
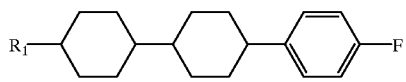 (3-1)
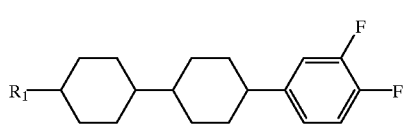 (3-2)
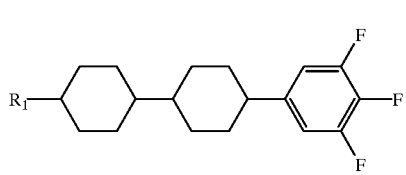 (3-3)
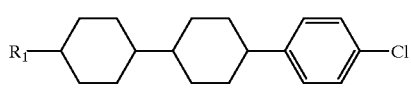 (3-4)
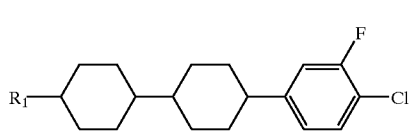 (3-5)
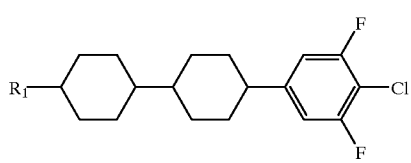 (3-6)
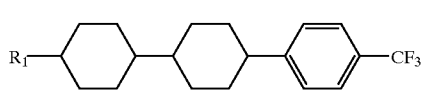 (3-7)
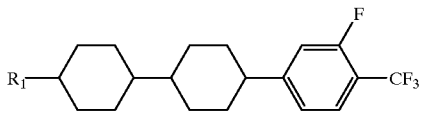 (3-8)
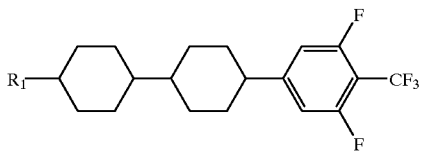 (3-9)
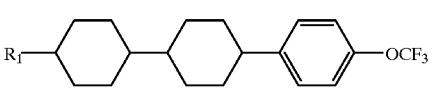 (3-10)
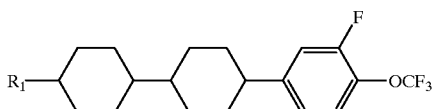 (3-11)
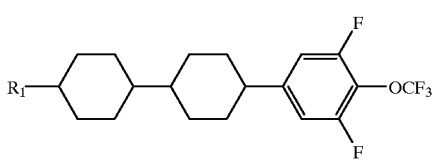 (3-12)
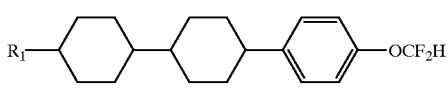 (3-13)
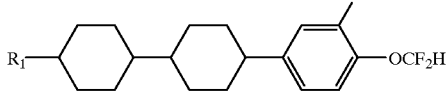 (3-14)
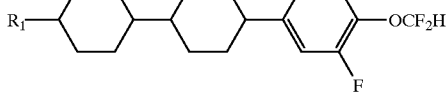 (3-15)
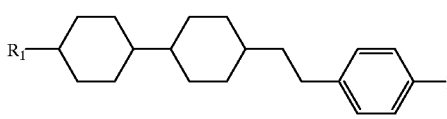 (3-16)
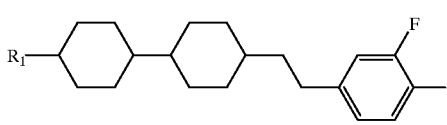 (3-17)
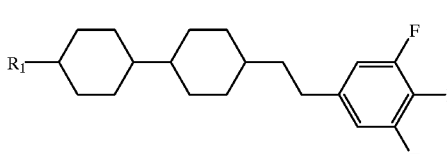 (3-18)

(3-19) 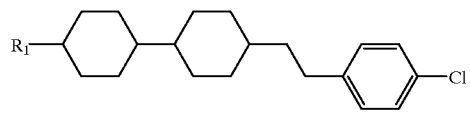
(3-20) 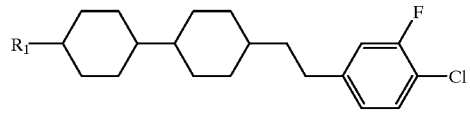
(3-21) 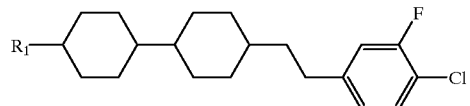
(3-22) 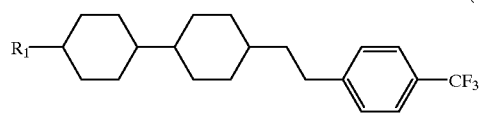
(3-23) 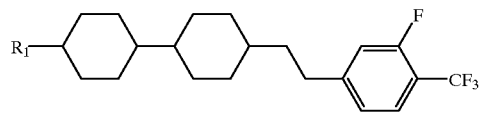
(3-24) 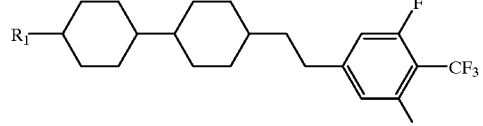
(3-25) 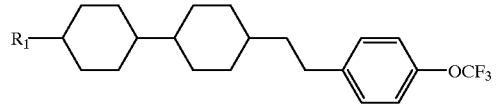
(3-26) 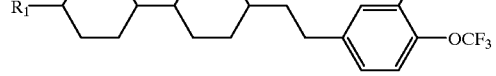
(3-27) 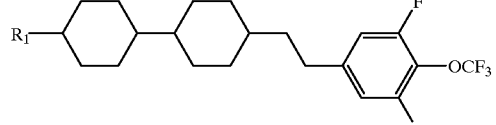
(3-28) 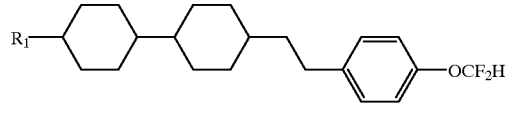
(3-29) 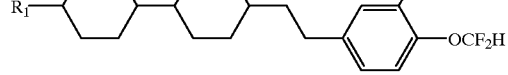
(3-30) 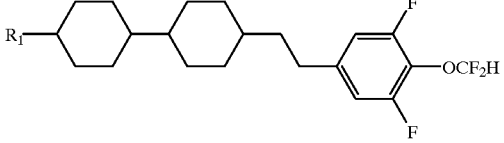
(3-31) 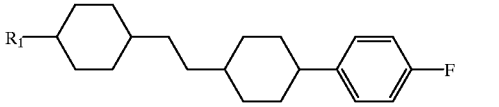
(3-32) 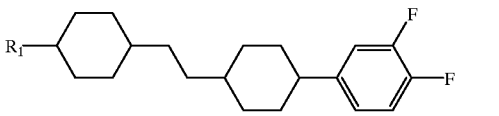
(3-33) 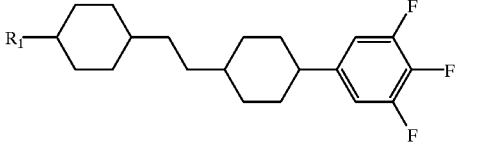
(3-34) 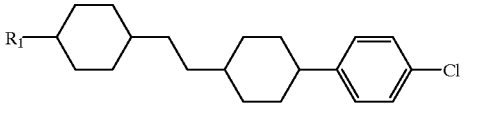
(3-35) 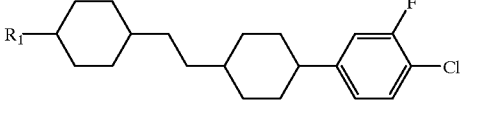
(3-36) 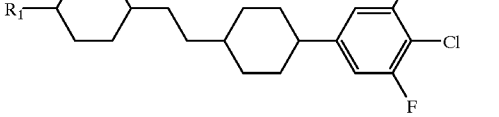
(3-37) 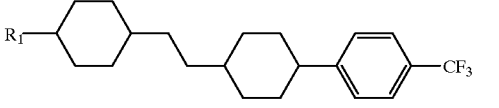
(3-38) 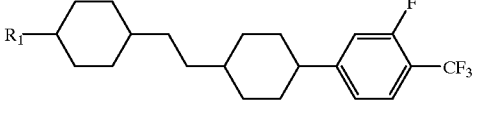
(3-39) 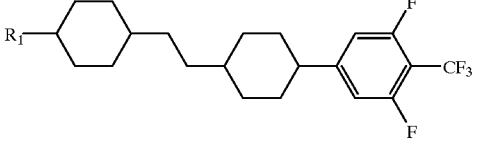

(3-40)
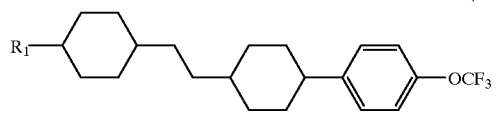
(3-41)
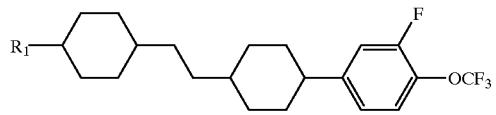
(3-42)
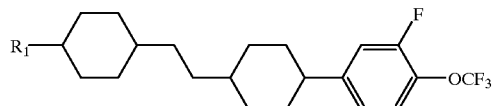
(3-43)
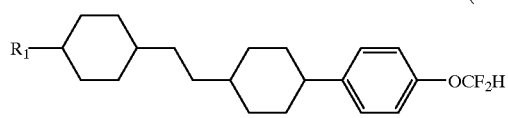
(3-44)
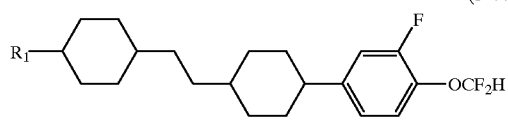
(3-45)
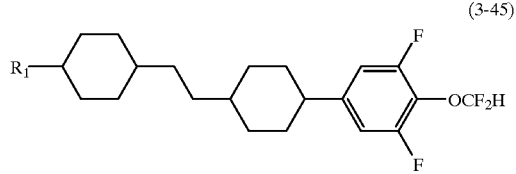
(3-46)
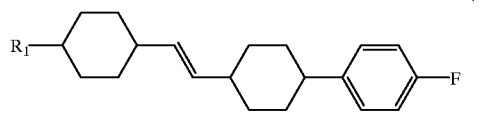
(3-47)
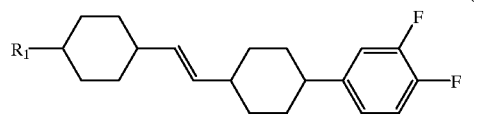
(3-48)
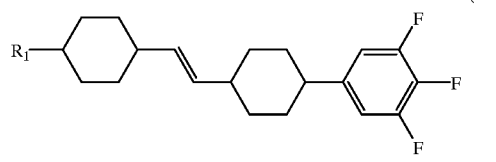
(4-1)
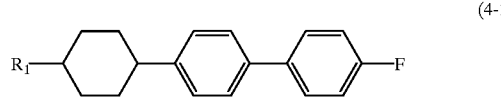
(4-2)
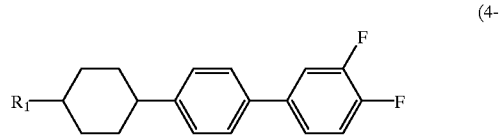
(4-3)
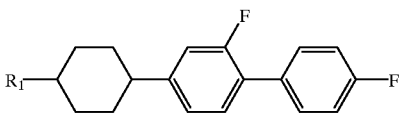
(4-4)
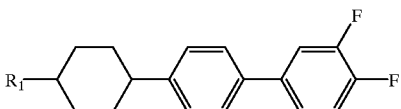
(4-5)
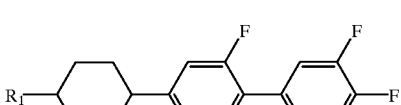
(4-6)
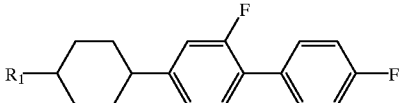
(4-7)
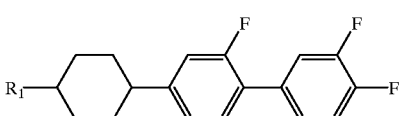
(4-8)
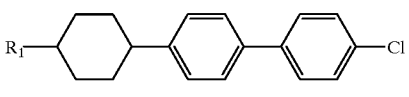
(4-9)
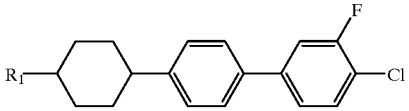
(4-10)
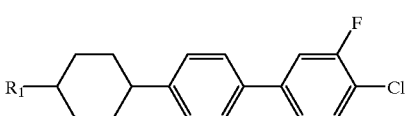
(4-11)
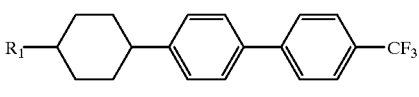
(4-12)
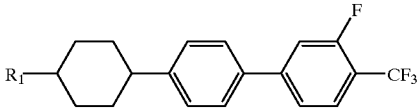
(4-13)
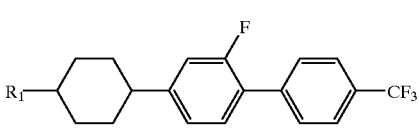

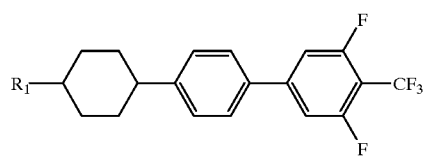 (4-14)
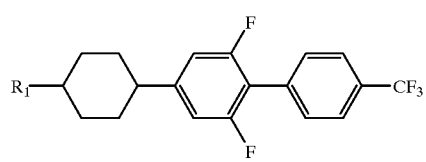 (4-15)
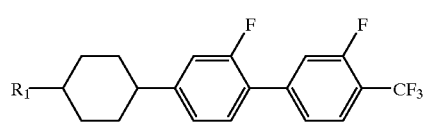 (4-16)
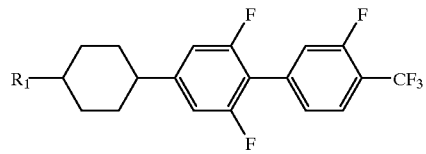 (4-17)
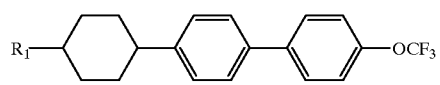 (4-18)
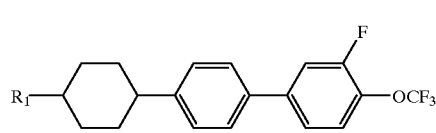 (4-19)
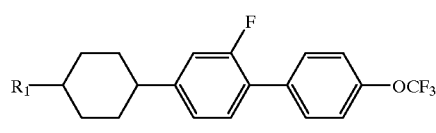 (4-20)
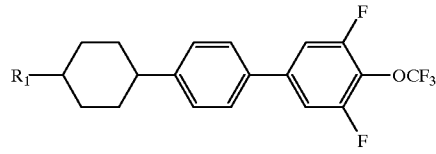 (4-21)
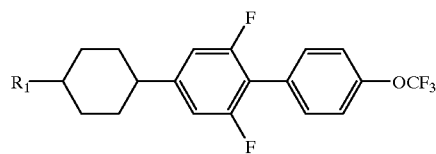 (4-22)
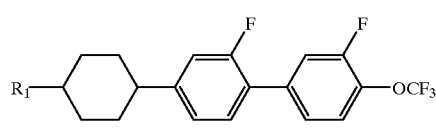 (4-23)
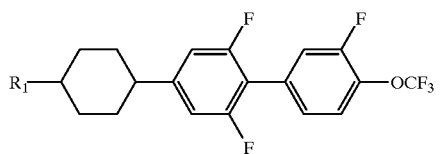 (4-24)
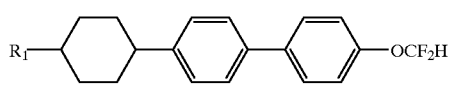 (4-25)
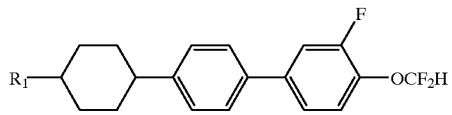 (4-26)
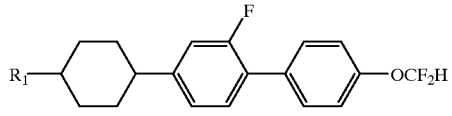 (4-27)
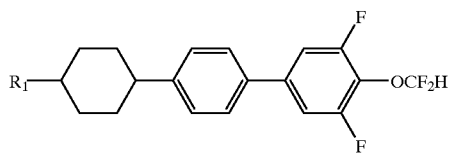 (4-28)
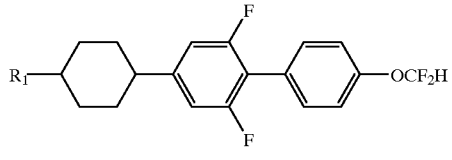 (4-29)
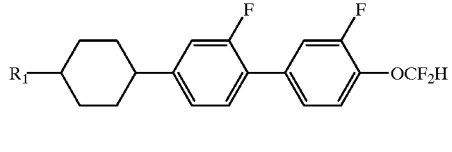 (4-30)
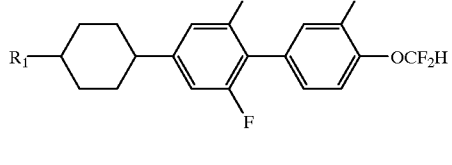 (4-31)
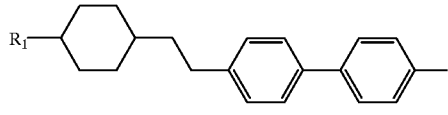 (4-32)
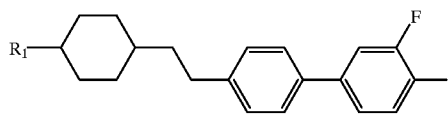 (4-33)

(4-34) 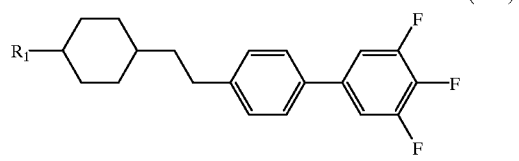
(4-35) 
(4-36) 
(4-37) 
(4-38) 
(4-39) 
(4-40) 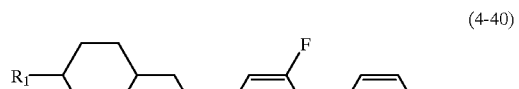
(4-41) 
(4-42) 
(4-43) 
(4-44) 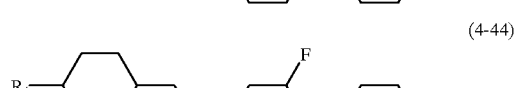
(4-45) 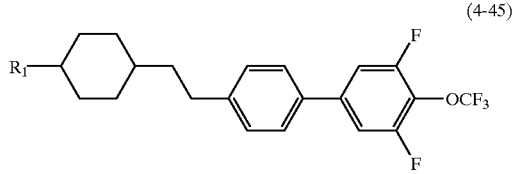
(4-46) 
(4-47) 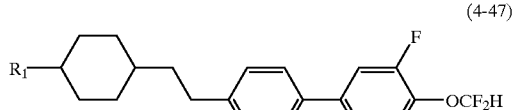
(4-48) 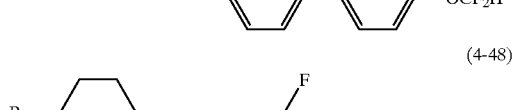
(4-49) 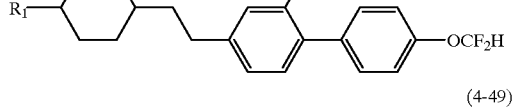
(4-50) 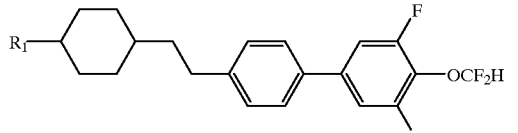
(4-51) 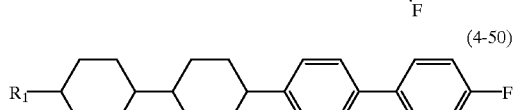
(4-52) 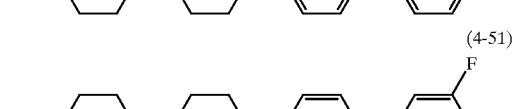
(4-53) 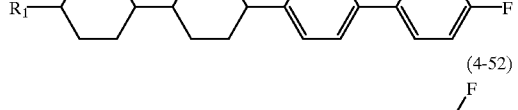
(4-54) 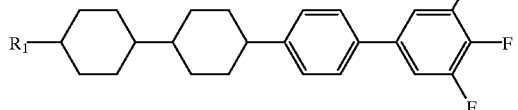
(4-55) 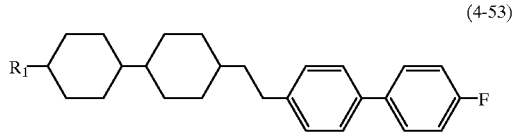

wherein $R_1$ has the same meaning as that described above.

Compounds expressed by one of the general formulas (2) to (4) exhibit a positive $\Delta\epsilon$, and are very excellent in heat stability and chemical stability.

Amount of the compounds to be used is suitably 1 to 99% by weight, preferably 10 to 97% by weight, and more desirably 40 to 95% by weight based on the total amount of liquid crystal composition.

Next, as preferable examples of the compounds included in one of the general formulas (5), (6), and (7) among the second B component, the compounds expressed by one of the formulas (5-1) to (5-24), (6-1) to (6-3), and (7-1) to (7-28) can be mentioned, respectively.

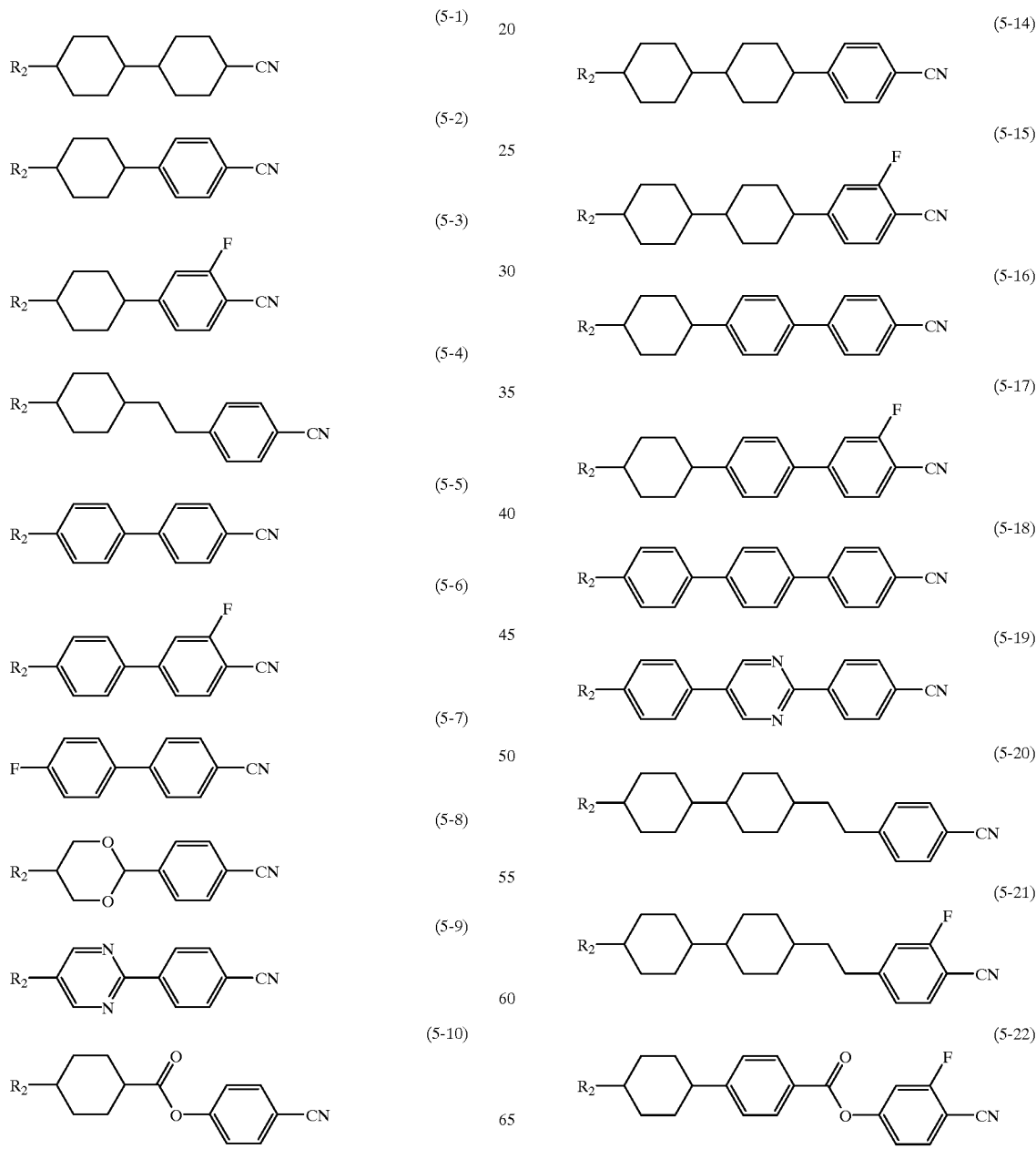

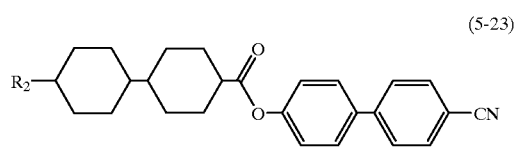
(5-23)
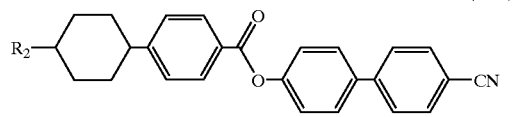
(5-24)
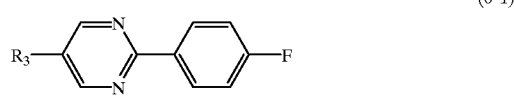
(6-1)
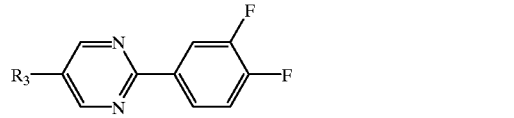
(6-2)
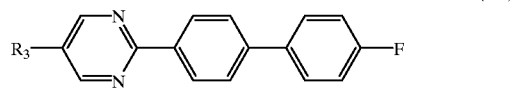
(6-3)
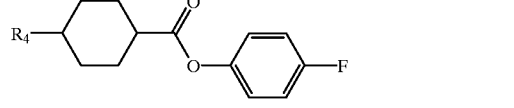
(7-1)
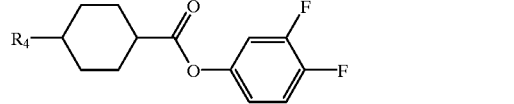
(7-2)
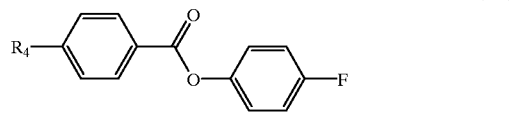
(7-3)
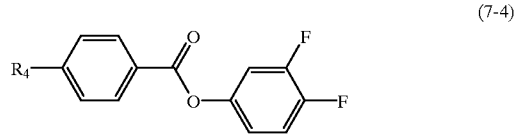
(7-4)
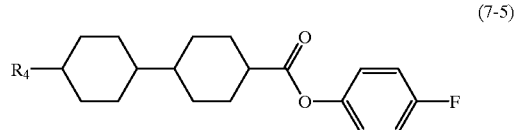
(7-5)
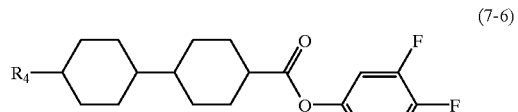
(7-6)
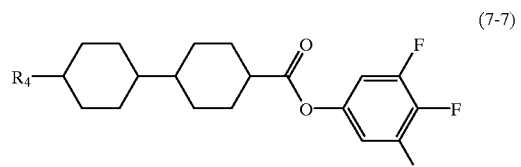
(7-7)
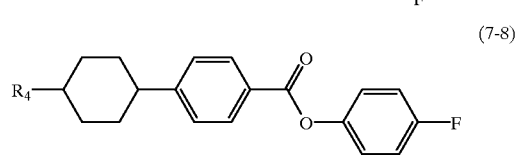
(7-8)
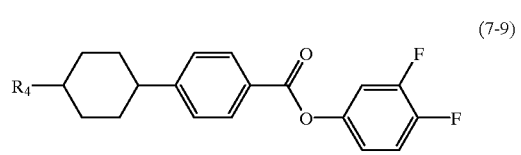
(7-9)
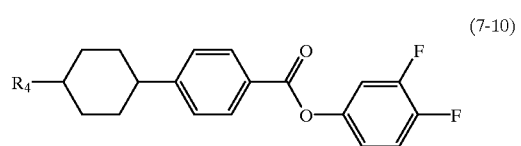
(7-10)
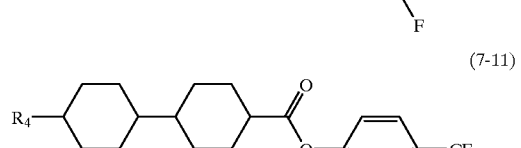
(7-11)
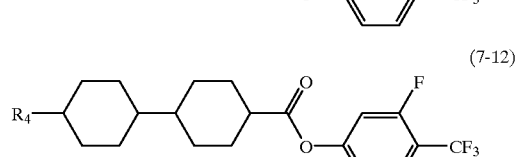
(7-12)
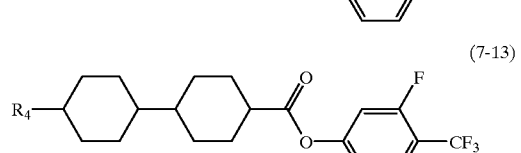
(7-13)
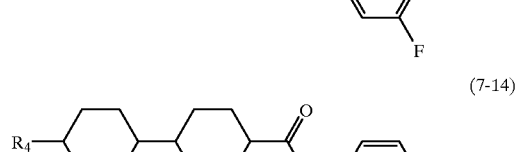
(7-14)
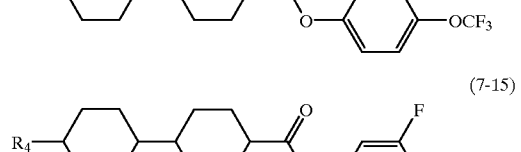
(7-15)
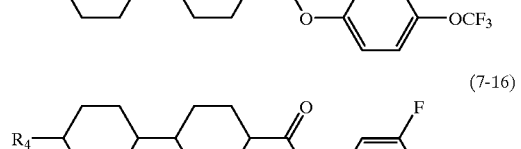
(7-16)
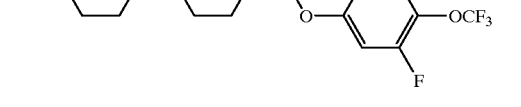

(7-17) 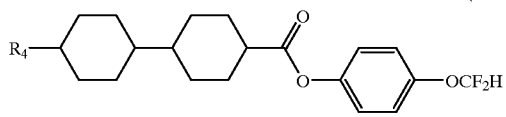

(7-18) 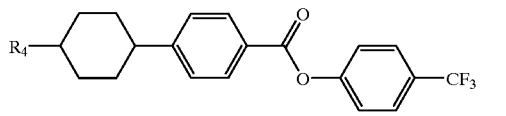

(7-19) 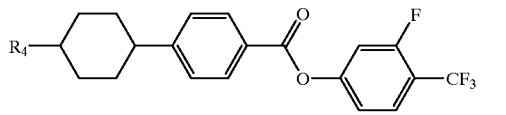

(7-20) 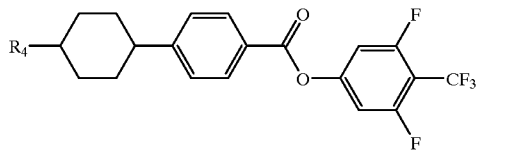

(7-21) 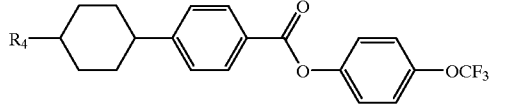

(7-22) 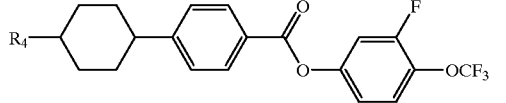

(7-23) 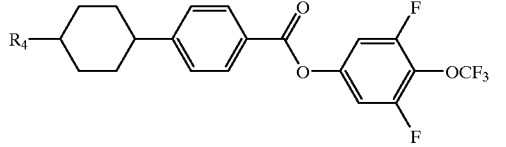

(7-24) 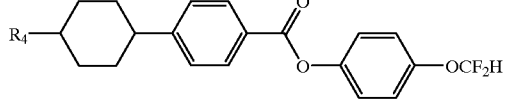

(7-25) 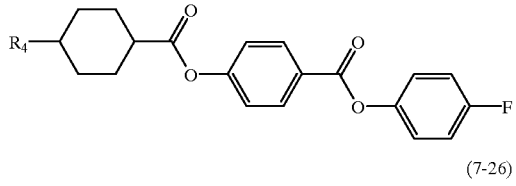

(7-26) 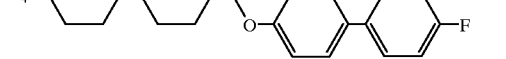

(7-27) 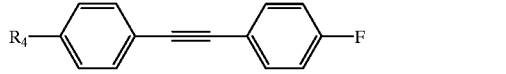

(7-28) 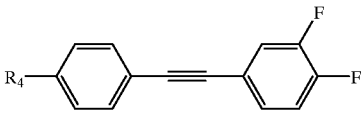

wherein $R_2$, $R_3$, and $R_4$ have the same meaning as described above.

Compounds expressed by one of the general formulas (5) to (7) have a large positive value of $\Delta\epsilon$, and are used as a component of the compositions particularly for the purpose of lowering $V_{th}$. The compounds are used also for the purpose of adjusting viscosity, for the purpose of adjusting $\Delta n$ and expanding the temperature range of a liquid crystal phase, and further for the purpose of improving the steepness.

As preferable examples of the compounds included in the general formula (8) or (9) among the second B component, the compounds expressed by one of the formulas (8-1) to (8-8), and (9-1) to (9-13) can be mentioned, respectively.

(8-1) 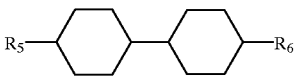

(8-2) 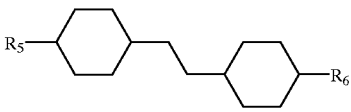

(8-3) 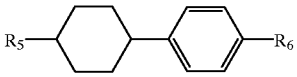

(8-4) 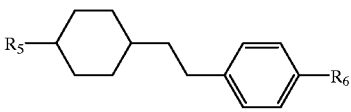

(8-5) 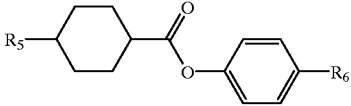

(8-6) 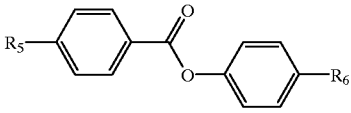

(8-7) 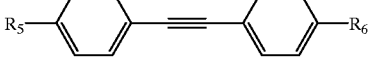

(8-8) 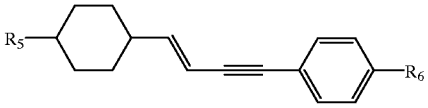

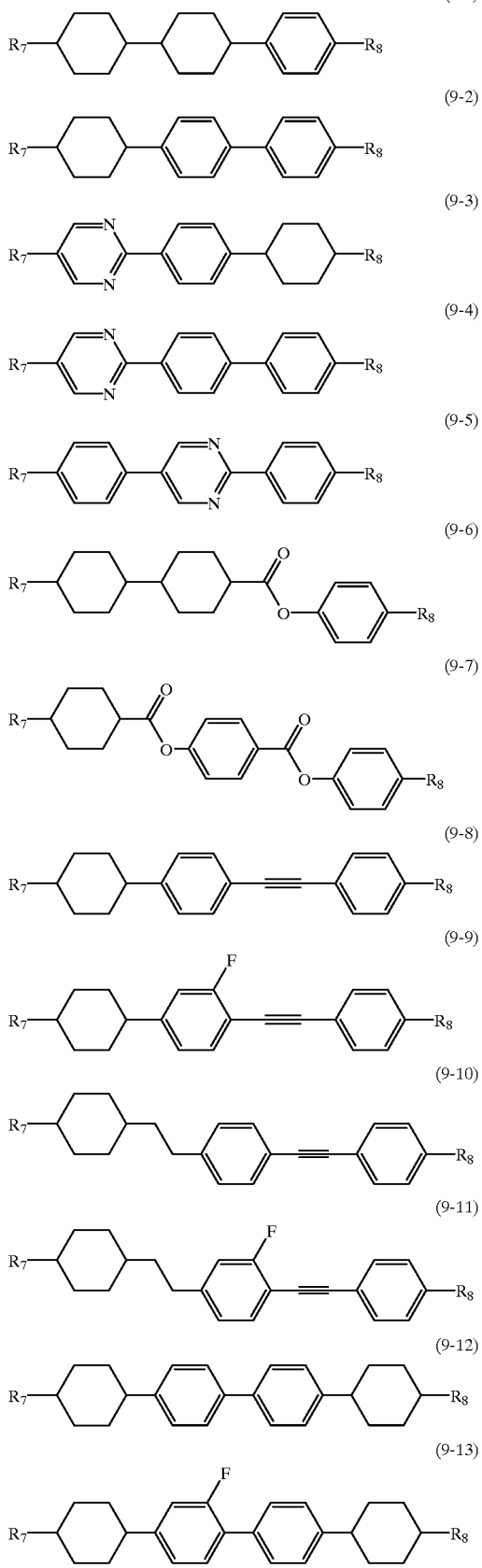

wherein $R_5$ and $R_6$ have the same meaning as those described above.

Compounds expressed by the general formula (8) or (9) have a negative or slightly positive $\Delta\epsilon$. Among them, the compounds expressed by the general formula (8) are used as a component of liquid crystal compositions for the purpose of principally reducing viscosity and/or adjusting An. Compounds expressed by the general formula (9) are used for the purpose of widening a nematic range such as raising clearing point and/or adjusting $\Delta n$.

Compounds expressed by one of the general formulas (5) to (9) are indispensable particularly when liquid crystal compositions for STN display mode or ordinary TN display mode are produced. While the compounds can be used in any amount in the range of 1 to 99% by weight when liquid crystal compositions for ordinary TN display mode or STN display mode are produced, the amount is preferably in the range of 10 to 97% by weight and more desirably in the range of 40 to 95% by weight. Also at that time, compounds expressed by one of the general formulas (2) to (4) may be used together as a part of the compositions.

Liquid crystal compositions provided by the present invention preferably comprise at least one liquid crystalline compounds expressed by the general formula (1) in the ratio of 0.1 to 99.9% by weight to develop excellent properties. The liquid crystal compositions are produced by methods which are conventional by themselves. For instance, the compositions are generally produced by methods such as a method in which various components are dissolved with one another at a high temperature, and a method in which components are dissolved and mixed in an organic solvent for the components and then the solvent is distilled off under a reduced pressure.

Also, the compositions of the present invention are improved and optimized due to their intended uses by adding a suitable additive when necessary. Such an additive is well known in the art and described in the literature in detail.

Further, the liquid crystal compositions can be used as ones for guest-host (GH) mode when a dichroic dye such as merocyanine type, styryl type, azo type, azomethine type, azoxy type, quinophthalone type, anthraquinone type, or tetrazine type is added. The liquid crystal compositions of the present invention can be used for liquid crystal compositions of an electrically controlled birefringence (ECB) mode or dynamic scattering (DS) mode including for NCAP which is prepared by the microencapsulation of a nematic liquid crystal and for polymer dispersed liquid crystal display devices (PDLCD) represented by polymer net work liquid crystal display devices (PNLCD) prepared by forming a polymer of three-dimensional reticulated structure in a liquid crystal.

As examples of the nematic liquid crystal compositions comprising the compound of the present invention, the following Composition Examples 1 through 15 can be mentioned.

In each of the following composition examples, compounds are indicated according to the instructions shown in Table 1 below. That is, left hand side terminal groups are indicated by s-, sO-, sOt-, Vs-, sVt-, V-, sV-, or FsV (both s and t are an integer of 1 or greater); bonding groups by 2, E, T, or V; ring structures by B, B(F), B(F,F), H, Py, or D; and right hand side terminal groups are indicated by -F, -CL, -C, -OCF$_3$, -OCF$_2$H, -w, -Ow, -wOx, -EMe, -V, -Vw, -wV, or -wVx (both w and x are an integer of 1 or greater), respectively. In the followings, the compound number added to some of the compounds are used to indicate the fact that the compounds having the same number in the following Composition Examples and Examples below are the same.

TABLE 1

| Left side terminal group | Symbol | Bonding group | Symbol |
|---|---|---|---|
| $C_sH_{2s+1}$— | s— | —$CH_2CH_2$— | 2 |
| $C_sH_{2s+1}O$— | sO— | —COO— | E |
| $C_sH_{2s+1}OC_tH_{2t}$— | sOt— | —C≡C— | T |
| $CH_2$=$CHC_sH_{2s}$— | Vs— | —CH=CH— | V |
| $C_sH_{2s+1}CH$=$CHC_tH_{2t}$— | sVt— | | |
| $CH_2$=CH— | V— | | |
| $C_sH_{2s+1}CH$=CH— | sV— | | |
| $FC_sH_{2s}CH$=CH— | FsV— | | |

| Ring structure | Symbol | Right side terminal group | Symbol |
|---|---|---|---|
| 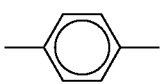 | B | —F<br>—Cl | —F<br>—CL |
| 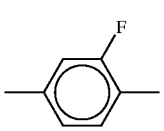 | B(F) | —CN<br>—$OCF_3$ | —C<br>—OCF3 |
| 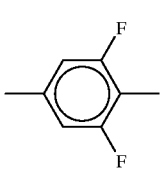 | B(F,F) | —$OCF_2H$<br>—$C_wH_{2w+1}$<br>—$OC_wH_{2w+1}$ | —OCF2H<br>—w<br>—Ow |
| 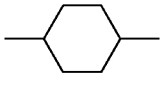 | H | —$C_wH_{2w}OC_xH_{2x+1}$ | —wOx |
| 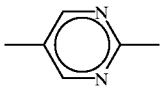 | Py | —$COOCH_3$<br>—CH=$CH_2$ | —EMe<br>—V |
| 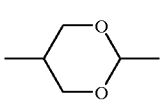 | D | —CH=$CHC_wH_{2w+1}$<br>—$C_wH_{2w}CH$=$CH_2$<br>—$C_wH_{2w}CH$=$CHC_xH_{2x+1}$ | —Vw<br>—wV<br>—wVx |

Composition Example 1

| F3V-HH-2V | (No. 11) | 5.0% |
|---|---|---|
| 3O1-BEB(F)-C | | 11.0% |
| V2-HB-C | | 11.0% |
| 3-HB-O2 | | 3.0% |
| 2-BTB-O1 | | 6.8% |
| 3-BTB-O1 | | 6.8% |
| 4-BTB-O1 | | 6.8% |
| 4-BTB-O2 | | 6.8% |
| 5-BTB-O1 | | 6.8% |
| 3-H2BTB-3 | | 3.0% |
| 3-H2BTB-4 | | 3.0% |
| 3-HB(F)TB-2 | | 6.0% |
| 3-HB(F)TB-3 | | 6.0% |
| 3-HB(F)TB-4 | | 6.0% |
| 2-PyBH-3 | | 4.0% |
| 3-PyBH-3 | | 4.0% |
| 3-PyBB-2 | | 4.0% |

Composition Example 2

| F3V-HH-2V | (No. 11) | 5.0% |
|---|---|---|
| F3V-HH-V1 | (No. 10) | 4.0% |
| F3V-HHH-V | (No. 69) | 3.0% |
| F3V-HBBH-V1 | (No. 190) | 3.0% |
| V2-HB-C | | 9.0% |
| 1V2-HB-C | | 9.0% |
| 3-HB-C | | 14.0% |
| 1O1-HB-C | | 8.0% |
| 2O1-HB-C | | 4.0% |
| 2-HHB-C | | 5.0% |
| 3-HHB-C | | 5.0% |
| 3-HH-4 | | 5.0% |
| 3-HH-EMe | | 3.0% |
| 1O1-HH-5 | | 4.0% |
| 2-BTB-O1 | | 11.0% |
| 3-HHB-1 | | 4.0% |
| 3-HHB-3 | | 4.0% |

Composition Example 3

| F3V-HH-2V | (No. 11) | 7.0% |
|---|---|---|
| F3V-HB-2V | (No. 31) | 8.0% |
| 2O1-BEB(F)-C | | 4.0% |
| 3O1-BEB(F)-C | | 12.0% |
| 5O1-BEB(F)-C | | 4.0% |
| 1V2-BEB (F,F)-C | | 15.0% |
| 3-HHEB-F | | 5.0% |
| 5-HHEB-F | | 5.0% |
| 3-HBEB-F | | 6.0% |
| 3-HHB-F | | 3.0% |
| 3-HHB-1 | | 8.0% |
| 3-HHB-3 | | 6.0% |
| 3-HHB-O1 | | 4.0% |
| 3-H2BTB-2 | | 4.0% |
| 3-H2BTB-3 | | 4.0% |
| 3-HB(F)VB-2 | | 5.0% |

Composition Example 4

| F3V-HH-V1 | (No. 10) | 5.0% |
|---|---|---|
| F3V-HH-2V | (No. 11) | 5.0% |
| F3V-HH-2V1 | (No. 12) | 4.0% |
| F3V-HHH-V1 | (No. 70) | 2.0% |
| F3V-HBH-2V1 | (No. 92) | 4.0% |
| 2-HB(F)-C | | 15.0% |
| 2-HEB-F | | 2.5% |
| 3-HEB-F | | 2.5% |
| 3-HHEB-F | | 5.0% |
| 5-HHEB-F | | 5.0% |
| 2-HHB(F)-C | | 10.0% |
| 3-HHB(F)-C | | 10.0% |
| 2-HHB(F)-F | | 10.0% |
| 3-HHB(F)-F | | 10.0% |
| 5-HHB(F)-F | | 10.0% |

Composition Example 5

| F3V-HH-2V | (No. 11) | 6.0% |
|---|---|---|
| F3V-HB-V | (No. 29) | 4.0% |
| F3V-HB-V1 | (No. 30) | 4.0% |
| F3V-HBBH-2V | (No. 191) | 3.0% |
| F3V-HBBB-V | (No. 209) | 3.0% |
| 3-HB(F)-C | | 4.0% |
| 3-HB-C | | 21.0% |
| 3-HHB-C | | 5.0% |
| 5-PyB-F | | 10.0% |
| 2-BTB-1 | | 6.0% |
| 3-HH-4 | | 5.0% |
| 3-HH-5 | | 5.0% |
| 3-HHB-1 | | 10.0% |
| 3-HHB-3 | | 10.0% |
| 3-HEBEB-2 | | 2.0% |
| 3-HEBEB-F | | 2.0% |

Composition Example 6

| F3V-HB-V | (No. 29) | 5.0% |
|---|---|---|
| F3V-HBH-2V | (No. 91) | 5.0% |
| 2-BB-C | | 8.0% |
| 4-BB-C | | 6.0% |
| 2-HB-C | | 10.0% |
| 3-HB-C | | 13.0% |

| | | |
|---|---|---|
| 3-HHB-F | | 5.0% |
| 2-HHB-C | | 5.0% |
| 3-HHB-C | | 6.0% |
| 5-PyB-F | | 6.0% |
| 3-PyBB-F | | 6.0% |
| 2-HHB-1 | | 5.0% |
| 3-HHB-1 | | 5.0% |
| 3-HHB-3 | | 10.0% |
| 3-HHB-O1 | | 5.0% |
| Composition Example 7 | | |
| F3V-HH-2V | (No. 11) | 5.0% |
| F3V-HB-2V1 | (No. 32) | 5.0% |
| 3-DB-C | | 10.0% |
| 4-DB-C | | 12.0% |
| 5-DB-C | | 8.0% |
| 2-BEB-C | | 10.0% |
| 5-PyB(F)-F | | 10.0% |
| 3-PyB-2 | | 2.0% |
| 3-PyB-O2 | | 2.0% |
| 3-HEB-O4 | | 5.0% |
| 4-HEB-O2 | | 3.0% |
| 3-HEB-O2 | | 2.0% |
| 1O-BEB-2 | | 2.0% |
| 5-HEB-1 | | 3.0% |
| 4-HEB-4 | | 3.0% |
| 3-HHB-3 | | 8.0% |
| 2-PyBH-3 | | 6.0% |
| 3-HBEBB-C | | 2.0% |
| 3-HHEBB-C | | 2.0% |
| Composition Example 8 | | |
| F3V-HH-2N | (No. 11) | 10.0% |
| 7-HB(F,F)-F | | 5.0% |
| 3-H2HB(F,F)-F | | 10.0% |
| 4-H2HB(F,F)-F | | 8.0% |
| 5-H2HB(F,F)-F | | 10.0% |
| 3-HHB(F,F)-F | | 8.0% |
| 3-HH2B(F,F)-F | | 12.0% |
| 5-HH2B(F,F)-F | | 10.0% |
| 3-HBB(F,F)-F | | 12.0% |
| 5-HBB(F,F)-F | | 10.0% |
| 3-HHBB(F,F)-F | | 2.0% |
| 3-HH2BB(F,F)-F | | 3.0% |
| Composition Example 9 | | |
| F3V-HH-2V | (No. 11) | 5.0% |
| F3V-HB-V | (No. 29) | 5.0% |
| F3V-HHH-V1 | (No. 70) | 2.0% |
| 7-HB(F)-F | | 12.0% |
| 2-HHB(F)-F | | 12.0% |
| 3-HHB(F)-F | | 12.0% |
| 5-HHB(F)-F | | 12.0% |
| 2-H2HB(F)-F | | 5.6% |
| 3-H2HB(F)-F | | 2.8% |
| 5-H2HB(F)-F | | 5.6% |
| 2-HBB(F)-F | | 6.5% |
| 3-HBB(F)-F | | 6.5% |
| 5-HBB(F)-F | | 13.0% |
| Composition Example 10 | | |
| F3V-HH-V | (No. 9) | 4.0% |
| F3V-HH-V1 | (No. 10) | 4.0% |
| F3V-HBBH-V | (No. 189) | 4.0% |
| 5-H2B(F)-F | | 5.0% |
| 2-HHB(F)-F | | 10.0% |
| 3-HHB(F)-F | | 10.0% |
| 5-HHB(F)-F | | 10.0% |
| 2-H2HB(F)-F | | 4.0% |
| 3-H2HB(F)-F | | 2.0% |
| 5-H2HB(F)-F | | 4.0% |
| 3-H2HB(F,F)-F | | 6.0% |
| 4-H2HB(F,F)-F | | 5.0% |
| 5-H2HB(F,F)-F | | 5.0% |
| 3-H2BB(F,F)-F | | 5.0% |
| 5-H2BB(F,F)-F | | 5.0% |
| 3-HHB(F,F)-F | | 8.0% |
| 3-HHEB(F,F)-F | | 6.0% |
| 5-HBEB(F,F)-F | | 3.0% |
| Composition Example 11 | | |
| F3V-HH-2V | (No. 11) | 4.0% |
| F3V-HB-2V | (No. 31) | 5.0% |
| F3V-HBH-V | (No. 89) | 3.0% |
| F3V-HBBB-2V | (No. 211) | 3.0% |
| 7-HB-CL | | 7.0% |
| 2-HBB(F)-F | | 5.0% |
| 3-HBB(F)-F | | 5.0% |
| 5-HBB(F)-F | | 10.0% |
| 4-H2BB(F)-F | | 6.0% |
| 5-H2BB(F)-F | | 6.0% |
| 2-HHB-CL | | 5.0% |
| 4-HHB-CL | | 10.0% |
| 3-HBB(F,F)-F | | 11.0% |
| 5-HBB(F,F)-F | | 10.0% |
| 3-HB(F)VB-2 | | 5.0% |
| 3-HB(F)VB-3 | | 5.0% |
| Composition Example 12 | | |
| F3V-HB-V1 | (No. 30) | 6.0% |
| F3V-HB-2V1 | (No. 32) | 4.0% |
| 2-HHB(F)-F | | 6.6% |
| 3-HHB(F)-F | | 6.7% |
| 5-HHB(F)-F | | 6.7% |
| 3-HHB(F,F)-F | | 7.0% |
| 5-HHB(F,F)-F | | 7.0% |
| 3-H2HB(F,F)-F | | 7.0% |
| 4-H2HB(F,F)-F | | 7.0% |
| 5-H2HB(F,F)-F | | 7.0% |
| 3-HH2B(F,F)-F | | 12.0% |
| 5-HH2B(F,F)-F | | 8.0% |
| 2-HBB-F | | 4.0% |
| 3-HBB-F | | 5.0% |
| 3-HHEBB-F | | 3.0% |
| 1O1-HBBH-3 | | 3.0% |
| Composition Example 13 | | |
| F3V-HH-2V | (No. 11) | 5.0% |
| F3V-HB-V1 | (No. 30) | 4.0% |
| F3V-HBBH-V | (No. 189) | 4.0% |
| 5-HB-F | | 7.0% |
| 5-HH-O1 | | 5.0% |
| 3-HHB-OCF2H | | 3.0% |
| 5-HHB-OCF2H | | 4.0% |
| 3-HHB(F,F)-OCF2H | | 10.0% |
| 5-HHB(F,F)-OCF2H | | 11.0% |
| 2-HHB-OCF3 | | 4.0% |
| 3-HHB-OCF3 | | 7.0% |
| 4-HHB-OCF3 | | 6.0% |
| 5-HHB-OCF3 | | 6.0% |
| 3-HH2B(F)-F | | 7.0% |
| 5-HH2B(F)-F | | 9.0% |
| 3-HHEB(F)-F | | 6.0% |
| 5-HB(F)BH-3 | | 2.0% |
| Composition Example 14 | | |
| F3V-HH-V | (No. 9) | 5.0% |
| F3V-HH-V1 | (No. 10) | 6.0% |
| F3V-HB-V | (No. 29) | 6.0% |
| F3V-HBBB-V1 | (No. 210) | 3.0% |
| V-HB-C | | 10.0% |
| 1V-HB-C | | 5.0% |
| 3-BB-C | | 5.0% |
| 5-BB-C | | 5.0% |
| 2-HB(F)-C | | 5.0% |
| 4-BB-3 | | 3.0% |
| 5-H2B-O2 | | 5.0% |
| 3-BEB-C | | 5.0% |
| 5-HEB-O3 | | 8.0% |
| 5-BBB-C | | 5.0% |
| 4-BPyB-C | | 4.0% |
| 4-BPyB-5 | | 4.0% |
| 5-HB2B-4 | | 4.0% |
| 5-HBB2B-3 | | 4.0% |
| 1V-HH-1O1 | | 4.0% |
| 1V2-HBB-3 | | 4.0% |
| Composition Example 15 | | |
| F3V-HH-2V | (No. 11) | 5.0% |

| | | |
|---|---|---|
| F3V-HHH-2V | (No. 71) | 2.0% |
| F3V-HBBH-V | (No. 189) | 3.0% |
| 4-HEB(F)-F | | 10.0% |
| 5-HEB(F)-F | | 8.0% |
| 2-BEB(F)-C | | 5.0% |
| 3-BEB(F)-C | | 5.0% |
| 4-BEB(F)-C | | 8.0% |
| 5-BEB(F)-C | | 8.0% |
| 1O3-HB(F)-C | | 6.0% |
| 3-HHEB(F)-F | | 5.0% |
| 5-HHEB(F)-F | | 5.0% |
| 2-HBEB(F)-C | | 5.0% |
| 3-HBEB(F)-C | | 5.0% |
| 4-HBEB(F)-C | | 5.0% |
| 5-HBEB(F)-C | | 5.0% |
| 3-HBTB-2 | | 4.0% |
| V2-HH-3 | | 3.0% |
| V2-HHB-1 | | 3.0% |
| Composition Example 16 | | |
| F3V-HH-V1F | (No. 242) | 5.0% |
| F2V-HB-2VF | (No. 251) | 5.0% |
| 3-DB-C | | 10.0% |
| 4-DB-C | | 12.0% |
| 5-DB-C | | 8.0% |
| 2-BEB-C | | 10.0% |
| 5-PyB(F)-F | | 10.0% |
| 3-PyB-2 | | 2.0% |
| 3-PyB-O2 | | 2.0% |
| 3-HEB-O4 | | 5.0% |
| 4-HEB-O2 | | 3.0% |
| 3-HEB-O2 | | 2.0% |
| 1O-BEB-2 | | 2.0% |
| 5-HEB-1 | | 3.0% |
| 4-HEB-4 | | 3.0% |
| 3-HHB-3 | | 8.0% |
| 2-PyBH-3 | | 6.0% |
| 3-HBEBB-C | | 2.0% |
| 3-HHEBB-C | | 2.0% |

Compounds of the present invention expressed by the general formula (1) can readily be produced by suitably selecting chemical procedures of ordinary organic synthesis, for example, those described in Organic Synthesis, Organic Reactions, or Jikken Kagaku Kouza (Course of Chemical Experiment), and using them in combination.

That is, methoxyethyltriphenylphosphonium halide (2) is first reacted with compound (1) in an ether type solvent such as THF and diethyl ether in the presence of a base such as sodium methylate, potassium-t-butoxide (t-BuOK), and butyl lithium to obtain compound (3) by using the Wittig reaction described, for instance, in Organic Reactions, Vol. 14, Chapter 3. Subsequently, the compound (3) is reacted with a mineral acid such as hydrochloric acid and sulfuric acid, or an organic acid such as formic acid, acetic acid, or p-toluenesulfonic acid to obtain aldehyde derivative (4), and then the aldehyde derivative (4) and alkyltriphenylphosphonium halide (5) are subjected to the Wittig reaction under the same conditions as those described above, to obtain intermediate compound (6).

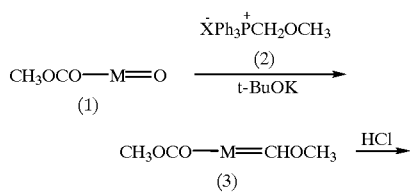

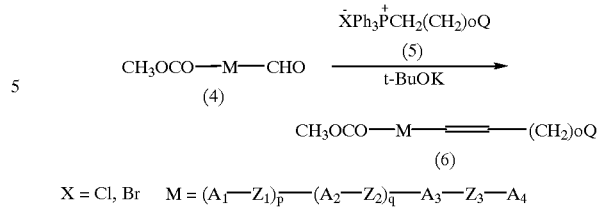

$X = Cl, Br \quad M = (A_1-Z_1)_{\overline{p}}-(A_2-Z_2)_{\overline{q}}-A_3-Z_3-A_4$ Also, compound (8) (wherein n is an integer of 1 to 5) can be obtained from the reaction between compound (1) and derivative of triphenylphosphonium halide (7) in the same manner as in the case where the compound (3) described above is obtained. Subsequently, the olefin portion of the compound (8) is reduced by a hydrogen-reduction in the presence of a reducing catalyst to obtain compound (9) and then a mineral acid such as hydrochloric acid and sulfuric acid, or an organic acid such as formic acid, acetic acid, and p-toluenesulfonic acid is reacted to the compound (9) to remove the protecting group thereby obtain aldehyde derivative (10). Thereafter, the aldehyde derivative (10) and alkyltriphenylphosphonium halide (5) are subjected to the Wittig reaction in the same manner as in the case where the compound (6) described above is obtained to produce intermediate compound (11).

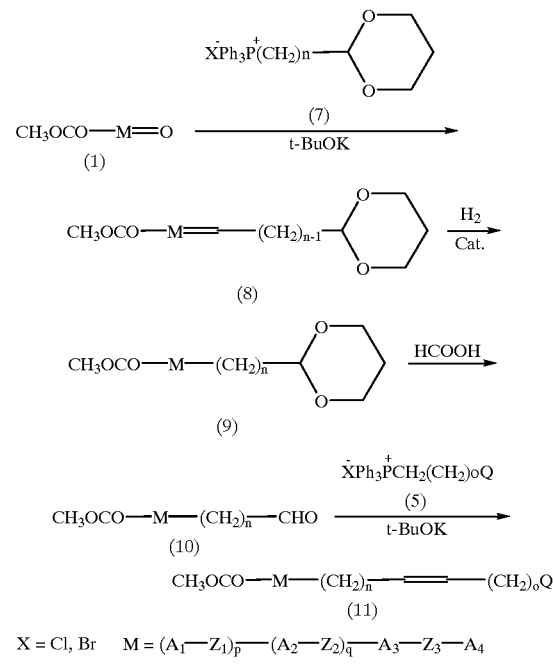

$X = Cl, Br \quad M = (A_1-Z_1)_{\overline{p}}-(A_2-Z_2)_{\overline{q}}-A_3-Z_3-A_4$ Compounds of the present invention can be produced by using the intermediate compound (6) or (11) described above.

That is, diisobutylaluminum hydride (hereinafter abbreviated as DIBAL) is first reacted to intermediate compound (6) to obtain aldehyde derivative (12), and then the same reaction as in the case where the compound (3) is obtained is repeatedly applied m times to the aldehyde derivative (12) to produce aldehyde derivative (13) in which number of methylene chain is increased by m. Then, the aldehyde derivative (13) and fluoroalkyltriphenylphosphonium halide (14) are subjected to the Wittig reaction to obtain compound (15), and then a mineral acid such as hydrochloric acid and sulfuric acid, and benzenesulfinic acid salt or p-toluenesulfinic acid salt is reacted to the compound to isomerize the compound thereby produce an example of the compounds of the present invention (1-1).

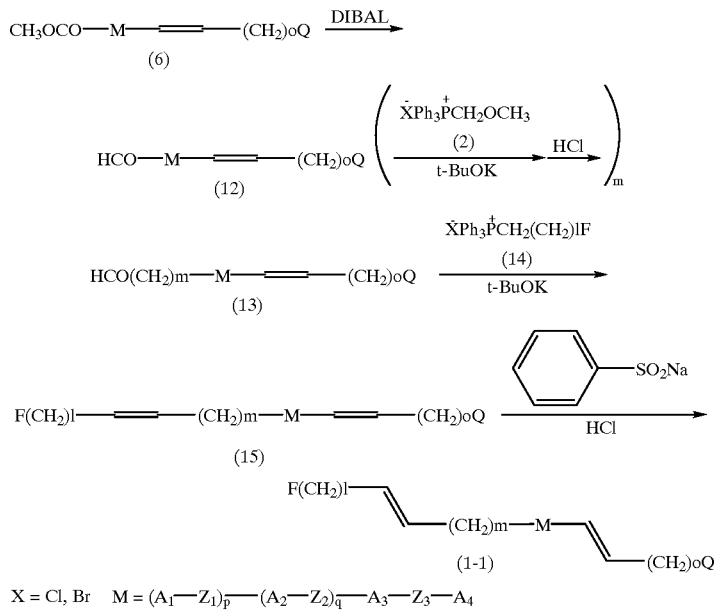

Also, another example of the compounds of the present invention (1-2) can be produced by conducting the same series of the procedures as in the case where the compound (1-1) is obtained with the exception that intermediate compound (11) is used in place of intermediate compound (6).

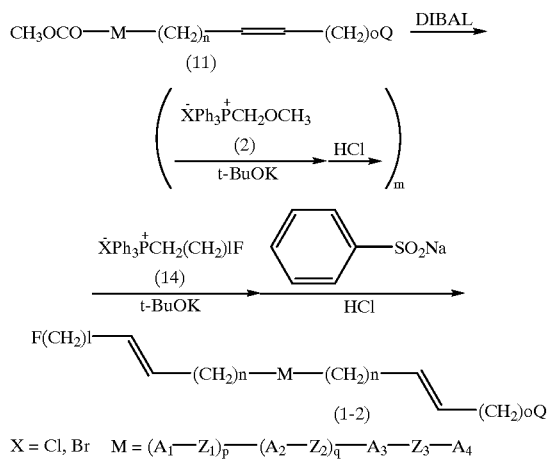

Now, the present invention will be described in more detail with reference to Examples. However, it should be understood that the present invention is by no means restricted to such specific Examples.

In each of the Examples, structure of compounds was confirmed by nuclear magnetic resonance spectrum (hereinafter abbreviated as $^1$H-NMR) and/or mass spectrum (hereinafter abbreviated as MS). In MS, M+ indicates molecular ion peak and the numeral in parenthesis indicates ion strength, respectively. Further, Cr indicates a crystal phase, S a smectic phase, N a nematic phase, and. Iso indicates an isotropic liquid phase, and all unit of phase transition temperature is ° C.

EXAMPLE 1

Preparation of 1-(3-butenyl)-trans-4-(trans-4-((E) -(5-fluoro-1-pentenyl)cyclohexyl)cyclohexane (Compound expressed by the general formula (1) wherein both rings $A_3$ and $A_4$ represent trans-1,4-cyclohexylene group, $Z_3$ represents a single bond, l is 3, both m and o are 0, n is 2, and both p and q are 0 (Compound No. 11))

First stage

After a mixture of 247.8 g (545.4 mmol) of 2-(1,3-dioxane-2-yl)ethyltriphenylphosphonium bromide and 2500 ml of THF was cooled down to −50° C. under nitrogen gas stream, 67.3 g (599.8 mmol) of t-BuOK was added thereto and stirred for 1 hour. To the mixture was added dropwise a solution of 100.0 g (419.6 mmol) of trans-4-(4-cyclohexanone-1-yl)cyclohexane carboxylic acid methyl ester in 1000 ml of THF while maintaining a temperature below −50° C. After the finish of the dropping, the reaction temperature was gradually raised up to room temperature and the mixture was further stirred for 5 hours. After the solvent was distilled off under a reduced pressure and 500 ml of water was added, it was extracted with 500 ml of toluene. After the organic layer thus obtained was washed with 200 ml of water thrice, the layer was dried over anhydrous magnesium sulfate. The solvent was distilled off under a reduced pressure and the residue was subjected to silica gel column chromatography (eluent: mixed solvent of ethyl acetate/heptane=1/9) to obtain 119.4 g of a crude derivative of cyclohexylidene (16).

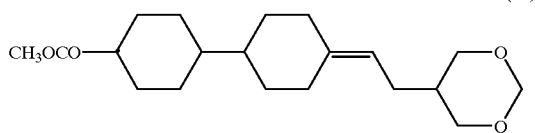

(16)

Second stage

After 119.4 g (357.0 mmol) of this crude product was dissolved in 1,200 ml of a mixed solvent of toluene/ethanol (4/1), a catalyst was added thereto and stirred at room temperature under a condition of hydrogen gas pressure of 1 to 2 kg/cm$^2$. When the amount of consumed hydrogen reached 8,000 ml, the stirring was terminated and the catalyst was filtered off. The solvent was distilled off under a reduced pressure, the residue was subjected to silica gel column chromatography (eluent: toluene and ethyl acetate), and the crude product thus obtained was recrystallized from a mixed solvent of ethyl acetate/Solmix/heptane (1/2/10) to obtain 74.9 g of trans-4-(trans-4-(2-(1,3-dioxane-2-yl)ethyl) cycloyhexyl)cyclohexane carboxylic acid methyl ester.

Third stage

This product in an amount of 74.9 g (221.2 mmol) was dissolved in 750 ml of toluene, 101.7 g (2.21 mmol) of formic acid was added thereto, heated to reflux for 5 hours, 600 ml of water was added, and then the liquid mixture thus obtained was separated into layers with a separating funnel. The organic layer thus obtained was washed with 600 ml of water thrice, dried over anhydrous magnesium sulfate, and then the solvent was distilled off under a reduced pressure to obtain 58.9 g of a crude trans.4-(trans-4-(2-formylethyl) cyclohexyl)cyclohexane carboxylic acid methyl ester.

Fourth stage

A solution of 58.9 g (210.0 mmol) of this product in 500 ml of THF was added dropwise, while maintaining a temperature below −50° C., to the following mixture, that is, the mixture obtained by cooling a liquid mixture of 97.5 g (272.9 mmol) of methyltriphenylphosphonium bromide with 1,000 ml of THF down to −50° C. under nitrogen gas stream, adding 33.7 g (300.3 mmol) of t-BuOK thereto, and stirring them for 1 hour. After the finish of the dropping, the reaction temperature was gradually raised up to room temperature, and further shirred for 5 hours. The solvent was distilled off under a reduced pressure, 250 ml of water was added to the residue, and then extracted with 250 ml of toluene. After the organic layer thus obtained was washed with 100 ml of water thrice and dried over anhydrous magnesium sulfate, the solvent was distilled off under a reduced pressure, and then the residue was subjected to silica gel column chromatography (eluent: mixed solvent of ethyl acetate/heptane=1/1) to obtain 50.3 g of a crude trans-4-(trans-4-(3-butenyl)cyclohexyl)cyclohexane carboxylic acid methyl ester.

Fifth stage

This crude product in an amount of 50.3 g (180.7 mmol) was dissolved in 1,000 ml of toluene, and 181 ml of 1.0 M toluene solution of DIBAL was added dropwise thereto at a temperature below −50° C. under nitrogen gas stream. After stirred at the same temperature for 1 hour, the reaction solution was gradually poured into water to terminate the reaction. Subsequently, it was washed with 700 ml of water thrice and dried over anhydrous magnesium sulfate. The solvent was distilled off under a reduced pressure to obtain 27.0 g of a crude trans-4-(trans-4-(3-butenyl) cyclohexyl) cyclohexylcarbaldehyde.

Sixth stage

Solution of 27.0 g (108.7 mmol) of this product in 300 ml of THF was added dropwise, while maintaining a temperature below −50° C., to the following mixture, that is, the mixture obtained by cooling a liquid mixture of 58.3 g (139.7 mmol) of 4-fluorobutyltriphenylphosphonium bromide with 600 ml of THF down to −50° C. under nitrogen gas stream, adding 17.3 g (154.2 mol) of t-BuOK, and stirring for 1 hour. After the finish of the dropping, the reaction temperature was gradually raised up to room temperature and further stirred for 5 hours. The solvent was distilled off under a reduced pressure, 150 ml of water was added thereto, and extracted with 150 ml of toluene. The organic layer thus obtained was washed with 50 ml of water thrice and dried over anhydrous magnesium sulfate. The solvent was distilled off under a reduced pressure and the residue was subjected to silica gel column chromatography (eluent: heptane) to obtain 23.7 g of a crude 1-(3-butenyl)-trans-4-(trans-4-((5-fluoro-1-pentenyl)cyclohexyl) cyclohexane.

Seventh stage

This crude product in an amount of 23.7 g (77.3 mmol) was dissolved in 250 ml of ethanol, 20.9 g (116.0 mmol) of sodium benzenesulfinate and 19 ml of 6N-hydrochloric acid were added thereto and heated to reflux for 4 hours. The solvent was distilled off under a reduced pressure, 100 ml of water was added to the residue, and then the residue was extracted with 150 ml of ethyl acetate. The organic layer was washed with 70 ml of water thrice, dried over anhydrous magnesium sulfate, the solvent was distilled off under a reduced pressure, and the residue was subjected to silica gel column chromatography (eluent: heptane) to obtain a crude product of 1-(3-butenyl)-trans-4-(trans-4-((E)-(5-fluoro-1-pentenyl)cyclohexyl) cyclohexane. This crude product was recrystallized from Solmix to obtain 16.1 g (yield 12.5 %) of the subject compound.

Phase transition temperature: Cr below room temperature $S_B$ 81.8 Iso

MS: m/e=306 (M$^+$, 15%), 135 (62), 95 (73), 81 (100), 67 (81).

$^1$H-NMR: As shown in FIG. 1.

EXAMPLE 2

Preparation of 1-ethenyl-trans-4-(trans-4-(trans-4-((E)-(5-fluoro-1-pentenyl)cyclohexyl)cyclohexyl)cyclohexane (Compound expressed by the general formula (1) wherein rings $A_2$, $A_3$, and $A_4$ represent trans-1,4-cyclohexylene group, both $Z_2$ and $Z_3$ represent single bond, Q is 3, m, n, and o are 0, p is 0, and q is 1 (Compound No. 69))

First stage

Mixture of 139.1 g (405.8 mmol) of methoxymethyltriphenylphosphonium chloride with 1,500 ml of THF was cooled down to −50° C. under nitrogen gas stream, 50.1 g (446.5 mmol) of t-BuOK was added thereto, and stirred for 1 hour. To this mixture was added dropwise a solution of 100.0 g (312.0 mmol) of trans-4-(trans-4-(4-cyclohexanone-1-yl)cyclohexyl)cyclohexane carboxylic acid methyl ester in 1,000 ml of THF while maintaining a temperature below −50° C. After finishing of the dropping, the reaction temperature was gradually raised up to room temperature and it was further stirred for 5 hours. The solvent was distilled off under a reduced pressure, 500 ml of water was added thereto, and extracted with 500 ml of toluene. The organic layer thus obtained was washed with 200 ml of water thrice and dried over anhydrous magnesium sulfate. The solvent was distilled off under a reduced pressure and the residue was subjected to silica gel column chromatography (eluent: mixed solvent of ethyl acetate/heptane=2/9) to obtain 95.7 g of a crude cyclohexylidene derivative (17).

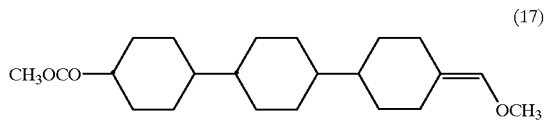
(17)

Second stage

After 95.7 g (274.6 mmol) of this crude product was dissolved in 1,000 ml of toluene, 126.6 g (2.76 mmol) of formic acid was added thereto and heated to reflux for 5 hours.

To this solution was added 500 ml of water, and the mixture was separated into layers with a separating funnel. The organic layer thus obtained was washed with 500 ml of water thrice, dried over anhydrous magnesium sulfate, and then the solvent was distilled under a reduced pressure to obtain 89.1 g of a crude trans-4-(trans-4-(trans-4-formylcyclohexyl)cyclohexyl) cyclohexane carboxylic acid methyl ester.

Third stage

Solution of 89.1 g (266.4 mmol) of this product in 900 ml of THF was added dropwise, while maintaining a temperature below −50° C., to the following mixture, that is, the mixture obtained by cooling a liquid mixture of 123.7 g (346.2 mmol) of methyltriphenylphosphonium bromide with 1,200 ml of THF down to −50° C. under nitrogen gas stream, adding 42.7 g (380.5 mmol) of t-BuOK, and stirring for 1 hour. After the finish of the dropping, the reaction temperature was gradually raised up to room temperature and further stirred for 5 hours. The solvent was distilled off under a reduced pressure, 300 ml of water was added to the residue, and extracted with 250 ml of toluene. The organic layer thus obtained was washed with 300 ml of water thrice and dried over anhydrous magnesium sulfate. The solvent was distilled off under a reduced pressure and the residue was subjected to silica gel column chromatography (eluent: mixed solvent of ethyl acetate/heptane=1/5) to obtain 70.9 g of a crude trans-4-(trans-4-(trans-4-ethenyl)cyclohexyl) cyclohexyl) cyclohexane carboxylic acid methyl ester.

Fourth stage

This crude product in an amount of 70.9 g (213.2 mmol) was dissolved in 1,500 ml of toluene, and 213 ml of 1.0 M toluene solution of DIBAL was added dropwise thereto while maintaining a temperature below −50° C. under nitrogen gas stream. After stirred at the same temperature for 1 hour, the reaction solution was gradually poured into water to terminate the reaction, washed with 1,000 ml of water thrice, and then dried over anhydrous magnesium sulfate. The solvent was distilled off under a reduced pressure to obtain 36.8 g of a crude trans-4-(trans-4-(trans-4-ethenylcyclohexyl)cyclohexyl) cyclohexylcarbaldehyde.

Fifth stage

Solution of 36.8 g (121.7 mmol) of this product in 350 ml of THF was added dropwise, while maintaining a temperature below −50° C., to the following mixture, that is, the mixture obtained by cooling a liquid mixture of 66.0 g (158.2 mmol) of 4-fluorobutyltriphenylphosphonium bromide with 700 ml of THF down to −50° C. under nitrogen gas stream, adding 19.5 g (173.8 mmol) of t-BuOK, and stirring for 1 hour. After the finish of the dropping, the reaction temperature was gradually raised up to room temperature, and further stirred for 5 hours. The solvent was distilled off under a reduced pressure, 200 ml of water was added thereto, and then extracted with 200 ml of toluene. The organic layer thus obtained was washed with 100 ml of water thrice, and dried over anhydrous magnesium sulfate. The solvent was distilled off under a reduced pressure, and the residue was subjected to silica gel column chromatography (eluent: heptane) to obtain 30.7 g of a crude 1-ethenyl-trans-4-(trans-4-(trans-4-((5-fluoro-1-pentenyl)cyclohexyl)cyclohexyl)cyclohexane.

Six stage

This crude product in an amount of 30.7 g (85.1 mmol) was dissolved in 300 ml of ethanol, 23.0 g (127.7 mmol) of sodium benzenesulfinate and 21 ml of 6N-hydrochloric acid were added thereto and then heated to reflux for 4 hours. The solvent was distilled off under a reduced pressure, 150 ml of water was added thereto, and then extracted with 200 ml of ethyl acetate. The organic layer thus obtained was washed with 100 ml of water thrice and then dried over anhydrous magnesium sulfate. The solvent was distilled off under a reduced pressure and the residue was subjected to silica gel column chromatography (eluent: heptane) to obtain a crude product of 1-ethenyl-trans-4-(trans-4-(trans-4-((E)-(5-fluoro-1-pentenyl)cyclohexyl)cyclohexyl)cyclohexane. This crude product was recrystallized from Solmix to obtain 19.9 g (yield 17.7%) of the subject compound.

MS: m/e=360 (M$^+$)

EXAMPLE 3

Preparation of 1-((E)-1-propenyl)-4-(4-(4-(trans-4-((E)-(5-fluoro-1-pentenyl)cyclohexyl)phenyl)phenyl)cyclohexane (Compound expressed by the general formula (1) wherein both rings $A_1$ and $A_4$ represent trans-1,4-cyclohexylene group, both rings $A_2$ and $A_3$ represent phenylene group, $Z_1$, $Z_2$ and $Z_3$ represent single bond, l is 3, both m and n are 0, o is 1, and both p and q are 1 (Compound No. 190))

First stage

Mixture of 114.1 g (332.8 mmol) of methoxymethyltriphenylphosphonium chloride with 1,000 ml of THF was cooled down to −50° C. under nitrogen gas stream, 41.1 g (366.3 mmol) of t-BuOK was added thereto, and then stirred for 1 hour.

To this mixture was added dropwise a solution of 100.0 g (256.1 mmol) of trans-4-(4-(4-(4-cyclohexanone-1-yl)phenyl)phenyl)cyclohexane carboxylic acid methyl ester in 1,000 ml of THF while maintaining a temperature below −50° C. After the finish of the dropping, the reaction temperature was gradually raised up to room temperature and further stirred for 5 hours. The solvent was distilled off under a reduced pressure, 500 ml of water was added thereto, and then extracted with 500 ml of toluene.

The organic layer thus obtained was washed with 200 ml of water thrice and then dried over anhydrous magnesium sulfate. The solvent was distilled off under a reduced pressure and the residue was subjected to silica gel column chromatography (eluent: toluene) to obtain 92.2 g of a crude cyclohexylidene derivative (18).

(18)

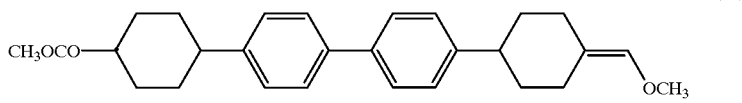

Second stage

After 92.2 g (220.3 mmol) of the crude product was dissolved in 1,000 ml of toluene, 101.3 g (2.20 mmol) of formic acid was added thereto and heated to reflux for 5 hours.

To this mixture was added 500 ml of water, the mixture was separated into layers with a separating funnel, and it was washed with 500 ml of water thrice and then dried over anhydrous magnesium sulfate. The solvent was distilled off under a reduced pressure to obtain 82.9 g of a crude trans-4-(4-(4-(trans-4-formylcyclohexyl)phenyl)phenyl)cyclohexane carboxylic acid methyl ester.

Third stage

Solution of 82.9 g (204.9 mmol) of this product in 800 ml of THF was added dropwise, while maintaining a temperature below −50° C., to the following mixture, that is, the mixture obtained by cooling a liquid mixture of 98.9 g (266.3 mmol) of ethyltriphenylphosphonium bromide with 1,000 ml of THF down to −50° C. under nitrogen gas stream, adding 29.9 g (266.5 mmol) of t-BuOK, and stirring for 1 hour. After the finish of the dropping, the reaction temperature was gradually raised up to room temperature and further stirred for 5 hours. The solvent was distilled off under a reduced pressure, 300 ml of water was added thereto, and then extracted with 250 ml of toluene. The organic layer thus obtained was washed with 300 ml of water thrice and then dried over anhydrous magnesium sulfate. The solvent was distilled off under a reduced pressure and the residue was subjected to silica gel column chromatography (eluent: toluene) to obtain 70.8 g of a crude trans-4-(4-(4-(trans-4-(1-propenyl)cyclohexyl)phenyl)phenyl)cyclohexane carboxylic acid methyl ester.

Fourth stage

This crude product in an amount of 70.8 g (169.9 mmol) was dissolved in 1,500 ml of toluene, and 170 ml of 1.0 M toluene solution of DIBAL was added dropwise thereto while maintaining a temperature below −50° C. under nitrogen gas stream. After stirred at the same temperature for 1 hour, the reaction solution was gradually poured into water to terminate the reaction, washed with 1,000 ml of water thrice, and then dried over anhydrous magnesium sulfate. The solvent was distilled off under a reduced pressure to obtain 40.1 g of a crude trans-4-(4-(4-(trans-4-(1-propenyl)cyclohexyl)phenyl)phenyl)cyclohexylcarbaldehyde.

Fifth stage Solution of 40.1 g (103.7 ml) of this product in 400 ml of THF was added dropwise, while maintaining a temperature below −50° C., to the following mixture, that is, the mixture obtained by cooling a liquid mixture of 56.3 g (134.9 mmol) of 4-fluorobutyltriphenylphosphonium bromide with 600 ml of THF down to −50° C., adding 16.6 g (147.9 mmol) of t-BuOK, and stirring for 1 hour. After the finish of the dropping, the reaction temperature was gradually raised up to room temperature and further stirred for 5 hours. The solvent was distilled off under a reduced pressure, 200 ml of water was added, and then extracted with 200 ml of toluene. The organic layer thus obtained was washed with 100 ml of water thrice and then dried over anhydrous magnesium sulfate. The solvent was distilled off under a reduced pressure and the residue was subjected to silica gel column chromatography (eluent: toluene) to obtain 31.4 g of a crude 1-(1-propenyl)-trans-4-(4-(4-(trans-4-((5-fluoro-1-pentenyl)cyclohexyl)phenyl)phenyl)cyclohexane.

Six stage

This crude product in an amount of 31.4 g (70.6 mmol) was dissolved in 300 ml of ethanol, 38.2 g (212.0 mmol) of sodium benzenesulfinate and 36 ml of 6N-hydrochloric acid were added thereto, and heated to reflux for 4 hours. The solvent was distilled off under a reduced pressure, 150 ml of water was added, and then extracted with 200 ml of ethyl acetate. The organic layer thus obtained was washed with 100 ml of water thrice and then dried over anhydrous magnesium sulfate. The solvent was distilled off under a reduced pressure and the residue was subjected to silica gel column chromatography (eluent: toluene) to obtain a crude product of 1-((E)-1-propenyl)-trans-4-(4-(4-(trans-4-((E)-(5-fluoro-1-pentenyl)cyclohexyl)phenyl)phenyl)cyclohexane. This crude product was recrystallized from Solmix to obtain 18.8 g (yield 16.5%) of the subject compound.

MS: m/e=444 (M$^+$)

According to the methods of Examples 1 to 3, the following compounds (Compound No. 1 to Compound No. 240) can be prepared. In the following Tables, each compound was designated by assuming that compounds expressed by the general formula (1) were decomposed into unit portions in turn and then making unit chemical formulas of specific compounds correspond to the unit portions. In the Tables, compounds (Compound Nos. 11, 69, and 190) obtained in Examples 1 to 3 are also shown together.

TABLE 2

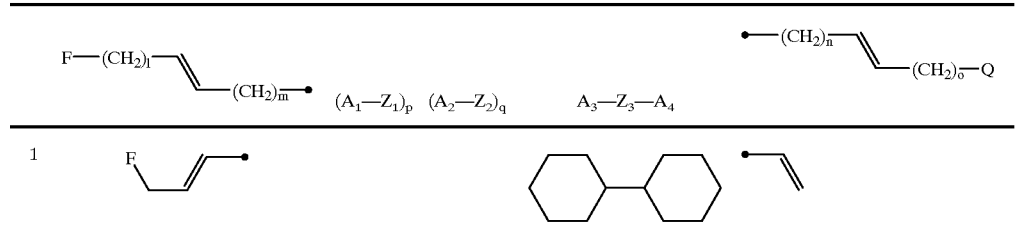

TABLE 2-continued
| | F—(CH$_2$)$_l$ —(CH$_2$)$_{\overline{m}}$• | (A$_1$—Z$_1$)$_p$ | (A$_2$—Z$_2$)$_q$ | A$_3$—Z$_3$—A$_4$ | •—(CH$_2$)$_{\overline{n}}$ (CH$_2$)$_o$—Q |
|---|---|---|---|---|---|
| 2 |  | | |  | 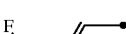 |
| 3 |  | | |  | |
| 4 |  | | |  | |
| 5 |  | | |  | |
| 6 |  | | |  | |
| 7 |  | | |  | |
| 8 |  | | |  | |
| 9 |  | | |  | |
| 10 |  | | |  | |
| 11 |  | | |  | * |
| 12 |  | | |  | |
| 13 |  | | |  | |
| 14 |  | | |  | |

TABLE 2-continued
| | F—(CH$_2$)$_l$〜(CH$_2$)$_{\overline{m}}$• | (A$_1$—Z$_1$)$_p$ | (A$_2$—Z$_2$)$_q$ | A$_3$—Z$_3$—A$_4$ | •—(CH$_2$)$_{\overline{n}}$〜(CH$_2$)$_o$—Q |
|---|---|---|---|---|---|
| 15 | 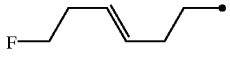 | | |  | 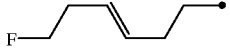 |
| 16 |  | | | 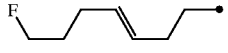 |  |
| 17 | 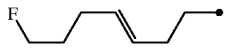 | | | 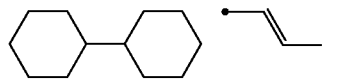 | 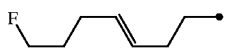 |
| 18 | 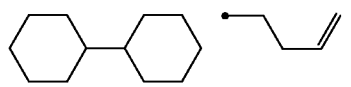 | | | 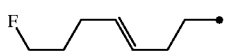 | 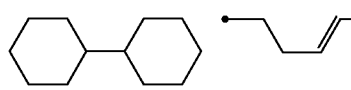 |
| 19 | 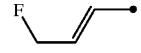 | | |  |  |
| 20 | 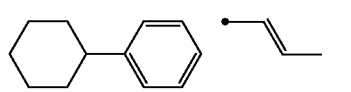 | | | 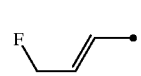 | 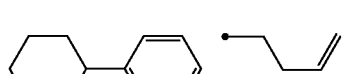 |
* Cr below room temperature S$_B$ 81.8 Iso
TABLE 3
| | F—(CH$_2$)$_l$〜(CH$_2$)$_{\overline{m}}$• | (A$_1$—Z$_1$)$_p$ | (A$_2$—Z$_2$)$_q$ | A$_3$—Z$_3$—A$_4$ | •—(CH$_2$)$_{\overline{n}}$〜(CH$_2$)$_o$—Q |
|---|---|---|---|---|---|
| 21 |  | | | 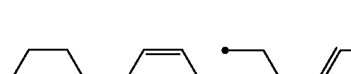 |  |
| 22 | 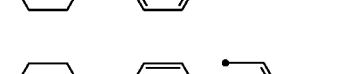 | | | | |
| 23 | | | | | |
| 24 | | | | | |
| 25 | | | | | |

TABLE 3-continued

| | F—(CH$_2$)$_l$—=—(CH$_2$)$_m$—• | (A$_1$—Z$_1$)$_p$ | (A$_2$—Z$_2$)$_q$ | A$_3$—Z$_3$—A$_4$ | •—(CH$_2$)$_n$—=—(CH$_2$)$_o$—Q |
|---|---|---|---|---|---|
| 26 | F–CH$_2$–CH=CH–• | | | Cy–Ph | •–CH=CH–CH$_3$ |
| 27 | F–CH$_2$–CH=CH–• | | | Cy–Ph | •–CH$_2$–CH=CH$_2$ |
| 28 | F–CH$_2$–CH=CH–• | | | Cy–Ph | •–CH$_2$–CH=CH–CH$_3$ |
| 29 | F–(CH$_2$)$_2$–CH=CH–• | | | Cy–Ph | •–CH=CH$_2$ |
| 30 | F–(CH$_2$)$_2$–CH=CH–• | | | Cy–Ph | •–CH=CH–CH$_3$ |
| 31 | F–(CH$_2$)$_2$–CH=CH–• | | | Cy–Ph | •–CH$_2$–CH=CH$_2$ |
| 32 | F–(CH$_2$)$_2$–CH=CH–• | | | Cy–Ph | •–CH$_2$–CH=CH–CH$_3$ |
| 33 | F–CH$_2$–CH=CH–CH$_2$–• | | | Cy–Ph | •–CH=CH$_2$ |
| 34 | F–CH$_2$–CH=CH–CH$_2$–• | | | Cy–Ph | •–CH=CH–CH$_3$ |
| 35 | F–CH$_2$–CH=CH–CH$_2$–• | | | Cy–Ph | •–CH$_2$–CH=CH$_2$ |
| 36 | F–CH$_2$–CH=CH–CH$_2$–• | | | Cy–Ph | •–CH$_2$–CH=CH–CH$_3$ |
| 37 | F–(CH$_2$)$_2$–CH=CH–CH$_2$–• | | | Cy–Ph | •–CH=CH$_2$ |
| 38 | F–(CH$_2$)$_2$–CH=CH–CH$_2$–• | | | Cy–Ph | •–CH=CH–CH$_3$ |
| 39 | F–(CH$_2$)$_2$–CH=CH–CH$_2$–• | | | Cy–Ph | •–CH$_2$–CH=CH$_2$ |

TABLE 3-continued

| | F—(CH$_2$)$_l$ —⟨CH=CH⟩— (CH$_2$)$_m$—• | (A$_1$—Z$_1$)$_p$ | (A$_2$—Z$_2$)$_q$ | A$_3$—Z$_3$—A$_4$ | •—(CH$_2$)$_n$—⟨CH=CH⟩—(CH$_2$)$_o$—Q |
|---|---|---|---|---|---|
| 40 | F–CH$_2$–CH$_2$–CH=CH–CH$_2$–• | | | cyclohexyl–phenyl | •–CH$_2$–CH=CH–CH$_3$ |

TABLE 4

| | F—(CH$_2$)$_l$ —⟨CH=CH⟩— (CH$_2$)$_m$—• | (A$_1$—Z$_1$)$_p$ | (A$_2$—Z$_2$)$_q$ | A$_3$—Z$_3$—A$_4$ | •—(CH$_2$)$_n$—⟨CH=CH⟩—(CH$_2$)$_o$—Q |
|---|---|---|---|---|---|
| 41 | F–CH=CH–• | | | cyclohexyl–CH$_2$CH$_2$–cyclohexyl | •–CH=CH$_2$ |
| 42 | F–CH=CH–• | | | cyclohexyl–CH$_2$CH$_2$–cyclohexyl | •–CH=CH–CH$_3$ |
| 43 | F–CH=CH–• | | | cyclohexyl–CH$_2$CH$_2$–cyclohexyl | •–CH$_2$–CH=CH$_2$ |
| 44 | F–CH=CH–• | | | cyclohexyl–CH$_2$CH$_2$–cyclohexyl | •–CH$_2$–CH=CH–CH$_3$ |
| 45 | F–CH$_2$–CH=CH–• | | | cyclohexyl–CH$_2$CH$_2$–cyclohexyl | •–CH=CH$_2$ |
| 46 | F–CH$_2$–CH=CH–• | | | cyclohexyl–CH$_2$CH$_2$–cyclohexyl | •–CH=CH–CH$_3$ |
| 47 | F–CH$_2$–CH=CH–• | | | cyclohexyl–CH$_2$CH$_2$–cyclohexyl | •–CH$_2$–CH=CH$_2$ |
| 48 | F–CH$_2$–CH=CH–• | | | cyclohexyl–CH$_2$CH$_2$–cyclohexyl | •–CH$_2$–CH=CH–CH$_3$ |
| 49 | F–CH$_2$CH$_2$–CH=CH–• | | | cyclohexyl–CH$_2$CH$_2$–cyclohexyl | •–CH=CH$_2$ |

TABLE 4-continued
| | F—(CH$_2$)$_l$ — (CH$_2$)$_{\overline{m}}$ — | (A$_1$—Z$_1$)$_p$ | (A$_2$—Z$_2$)$_q$ | A$_3$—Z$_3$—A$_4$ | —(CH$_2$)$_{\overline{n}}$ — (CH$_2$)$_{\overline{o}}$—Q |
|---|---|---|---|---|---|
| 50 | 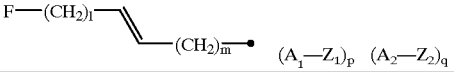 | | | 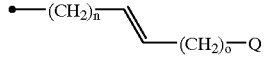 | 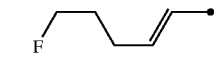 |
| 51 | 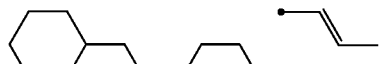 | | | 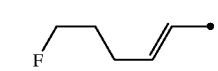 |  |
| 52 | 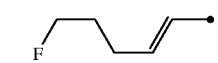 | | | 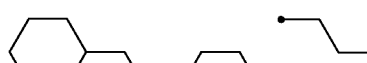 | 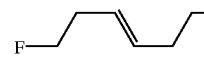 |
| 53 | 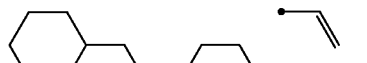 | | | 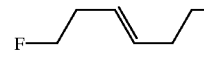 | 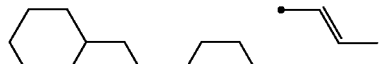 |
| 54 | 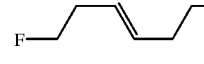 | | | 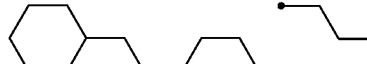 | 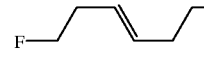 |
| 55 | 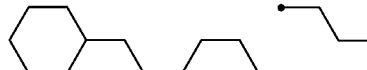 | | |  | 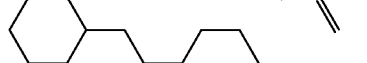 |
| 56 |  | | | 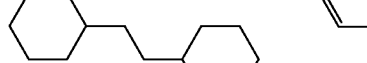 | 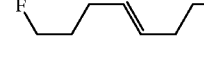 |
| 57 | 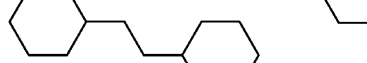 | | | 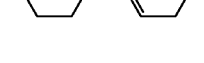 | 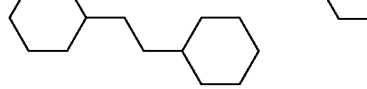 |
| 58 | | | | | |
| 59 | | | | | |
| 60 | | | | | |

TABLE 4-continued
| | F—(CH$_2$)$_l$—=—(CH$_2$)$_{\overline{m}}$—• | (A$_1$—Z$_1$)$_p$ | (A$_2$—Z$_2$)$_q$ | A$_3$—Z$_3$—A$_4$ | •—(CH$_2$)$_n$—=—(CH$_2$)$_o$—Q |
|---|---|---|---|---|---|
| 61 | 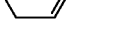 | |  | 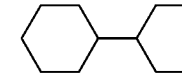 |  |
| 62 | 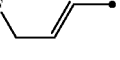 | |  | 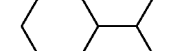 |  |
| 63 | 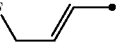 | |  | 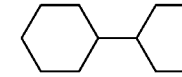 |  |
| 64 | 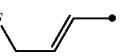 | |  | 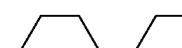 |  |
| 65 |  | |  | 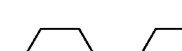 |  |
| 66 |  | |  | 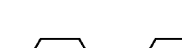 |  |
| 67 |  | |  |  |  |
| 68 |  | |  | 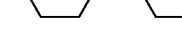 |  |
| 69 |  | |  |  |  |
| 70 | 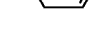 | |  | 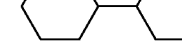 |  |
| 71 | 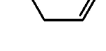 | |  | 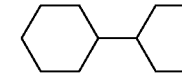 |  |
| 72 | 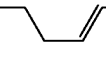 | |  | 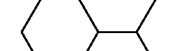 |  |
| 73 | 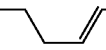 | |  | 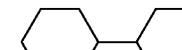 |  |
| 74 | 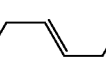 | |  | 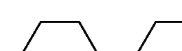 |  |

TABLE 4-continued
| | F—(CH₂)ₗ<br>‖<br>(CH₂)ₘ—• | (A₁—Z₁)ₚ | (A₂—Z₂)q | A₃—Z₃—A₄ | •—(CH₂)ₙ<br>‖<br>(CH₂)ₒ—Q |
|---|---|---|---|---|---|
| 75 |  | |  |  |  |
| 76 |  | |  |  | 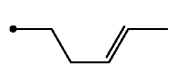 |
| 77 | 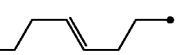 | |  |  |  |
| 78 | 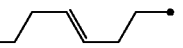 | |  | 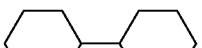 | 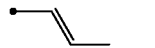 |
| 79 | 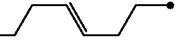 | |  | 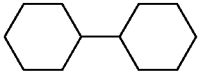 | 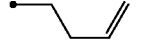 |
| 80 | 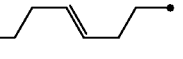 | |  | 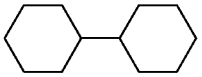 | 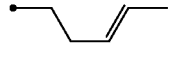 |
TABLE 6
| | F—(CH₂)ₗ<br>‖<br>(CH₂)ₘ—• | (A₁—Z₁)ₚ | (A₂—Z₂)q | A₃—Z₃—A₄ | •—(CH₂)ₙ<br>‖<br>(CH₂)ₒ—Q |
|---|---|---|---|---|---|
| 81 |  | |  | 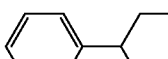 |  |
| 82 |  | |  |  |  |
| 83 | 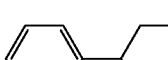 | |  |  |  |
| 84 |  | | 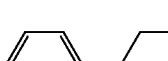 |  |  |
| 85 | 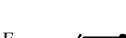 | |  | 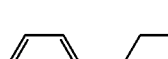 |  |
| 86 |  | |  |  |  |

TABLE 6-continued
| | F—(CH₂)ₗ—〰〰—(CH₂)ₘ—● | (A₁—Z₁)ₚ | (A₂—Z₂)q | A₃—Z₃—A₄ | ●—(CH₂)ₙ—〰〰—(CH₂)ₒ—Q |
|---|---|---|---|---|---|
| 87 |  |  | | 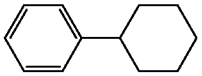 | 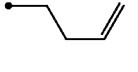 |
| 88 | 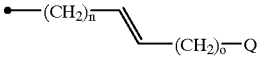 | 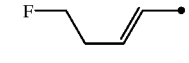 | |  | 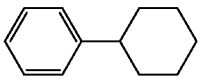 |
| 89 | 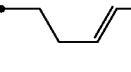 | 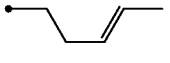 | | 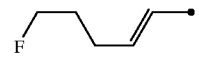 |  |
| 90 | 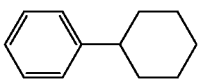 | 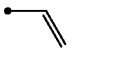 | |  | 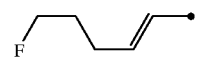 |
| 91 |  | 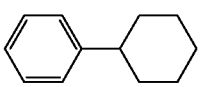 | | 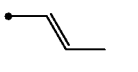 |  |
| 92 | 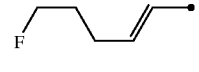 |  | | 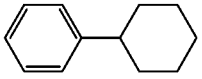 | 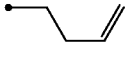 |
| 93 | 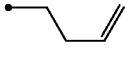 | 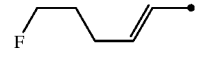 | |  | 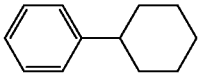 |
| 94 | 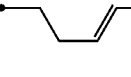 | 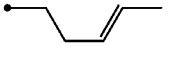 | | 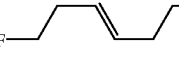 |  |
| 95 | 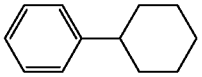 | 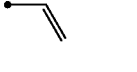 | |  | 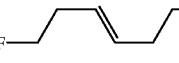 |
| 96 |  | 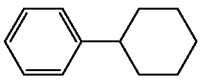 | | 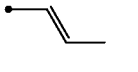 |  |
| 97 | 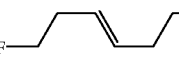 |  | | 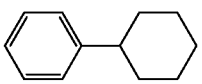 | 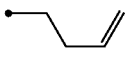 |
| 98 | 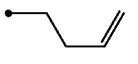 | 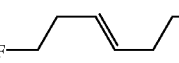 | |  | 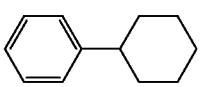 |
| 99 | 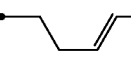 | 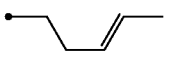 | | 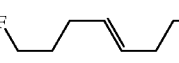 |  |
| 100 | 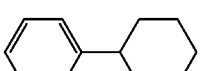 | 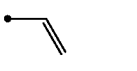 | |  | 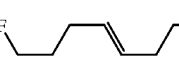 |

TABLE 7

| | F—(CH₂)ₗ—(CH₂)ₘ—• | (A₁—Z₁)ₚ | (A₂—Z₂)_q | A₃—Z₃—A₄ | •—(CH₂)ₙ—(CH₂)ₒ—Q |
|---|---|---|---|---|---|
| 101 | F–/=/–• | | ⬡ | ⌬–⌬ | •–/= |
| 102 | F–/=/–• | | ⬡ | ⌬–⌬ | •–/=/ |
| 103 | F–/=/–• | | ⬡ | ⌬–⌬ | •–\–/= |
| 104 | F–/=/–• | | ⬡ | ⌬–⌬ | •–\–/=/ |
| 105 | F–\–/=/–• | | ⬡ | ⌬–⌬ | •–/= |
| 106 | F–\–/=/–• | | ⬡ | ⌬–⌬ | •–/=/ |
| 107 | F–\–/=/–• | | ⬡ | ⌬–⌬ | •–\–/= |
| 108 | F–\–/=/–• | | ⬡ | ⌬–⌬ | •–\–/=/ |
| 109 | F–\–/=/–• | | ⬡ | ⌬–⌬ | •–/= |
| 110 | F–\–/=/–• | | ⬡ | ⌬–⌬ | •–/=/ |
| 111 | F–\–/=/–• | | ⬡ | ⌬–⌬ | •–\–/= |
| 112 | F–\–/=/–• | | ⬡ | ⌬–⌬ | •–\–/=/ |
| 113 | F–\–/=/\–• | | ⬡ | ⌬–⌬ | •–/= |
| 114 | F–\–/=/\–• | | ⬡ | ⌬–⌬ | •–/=/ |

TABLE 7-continued

| | F—(CH$_2$)$_l$—CH=CH—(CH$_2$)$_m$—• | (A$_1$—Z$_1$)$_p$ | (A$_2$—Z$_2$)$_q$ | A$_3$—Z$_3$—A$_4$ | •—(CH$_2$)$_n$—CH=CH—(CH$_2$)$_o$—Q |
|---|---|---|---|---|---|
| 115 | | cyclohexyl | | biphenyl | |
| 116 | | cyclohexyl | | biphenyl | |
| 117 | | cyclohexyl | | biphenyl | |
| 118 | | cyclohexyl | | biphenyl | |
| 119 | | cyclohexyl | | biphenyl | |
| 120 | | cyclohexyl | | biphenyl | |

TABLE 8

| | F—(CH$_2$)$_l$—CH=CH—(CH$_2$)$_m$—• | (A$_1$—Z$_1$)$_p$ | (A$_2$—Z$_2$)$_q$ | A$_3$—Z$_3$—A$_4$ | •—(CH$_2$)$_n$—CH=CH—(CH$_2$)$_o$—Q |
|---|---|---|---|---|---|
| 121 | | | cyclohexyl-CH$_2$CH$_2$- | bicyclohexyl | |
| 122 | | | cyclohexyl-CH$_2$CH$_2$- | bicyclohexyl | |
| 123 | | | cyclohexyl-CH$_2$CH$_2$- | bicyclohexyl | |
| 124 | | | cyclohexyl-CH$_2$CH$_2$- | bicyclohexyl | |
| 125 | | | cyclohexyl-CH$_2$CH$_2$- | bicyclohexyl | |
| 126 | | | cyclohexyl-CH$_2$CH$_2$- | bicyclohexyl | |

TABLE 8-continued

TABLE 9

| | F—(CH₂)ₗ—CH=CH—(CH₂)ₘ—• | (A₁—Z₁)ₚ | (A₂—Z₂)q | A₃—Z₃—A₄ | •—(CH₂)ₙ—CH=CH—(CH₂)ₒ—Q |
|---|---|---|---|---|---|
| 141 | F-CH=CH-• | | Cy-C₂H₄ | Ph-Cy | •-CH=CH₂ |
| 142 | F-CH=CH-• | | Cy-C₂H₄ | Ph-Cy | •-CH=CH-CH₃ |
| 143 | F-CH=CH-• | | Cy-C₂H₄ | Ph-Cy | •-CH₂-CH=CH₂ |
| 144 | F-CH=CH-• | | Cy-C₂H₄ | Ph-Cy | •-CH₂-CH=CH-CH₃ |
| 145 | F-CH₂-CH=CH-• | | Cy-C₂H₄ | Ph-Cy | •-CH=CH₂ |
| 146 | F-CH₂-CH=CH-• | | Cy-C₂H₄ | Ph-Cy | •-CH=CH-CH₃ |
| 147 | F-CH₂-CH=CH-• | | Cy-C₂H₄ | Ph-Cy | •-CH₂-CH=CH₂ |
| 148 | F-CH₂-CH=CH-• | | Cy-C₂H₄ | Cy-Cy | •-CH₂-CH=CH-CH₃ |
| 149 | F-CH₂-CH₂-CH=CH-• | | Cy-C₂H₄ | Cy-Cy | •-CH=CH₂ |
| 150 | F-CH₂-CH₂-CH=CH-• | | Cy-C₂H₄ | Cy-Cy | •-CH=CH-CH₃ |
| 151 | F-CH₂-CH₂-CH=CH-• | | Cy-C₂H₄ | Cy-Cy | •-CH₂-CH=CH₂ |
| 152 | F-CH₂-CH₂-CH=CH-• | | Cy-C₂H₄ | Cy-Cy | •-CH₂-CH=CH-CH₃ |
| 153 | F-CH₂-CH=CH-CH₂-• | | Cy-C₂H₄ | Cy-Cy | •-CH=CH₂ |
| 154 | F-CH₂-CH=CH-CH₂-• | | Cy-C₂H₄ | Cy-Cy | •-CH=CH-CH₃ |

TABLE 9-continued
| | F—(CH₂)ₗ﹇(CH₂)ₘ﹈ | (A₁—Z₁)ₚ | (A₂—Z₂)_q | A₃—Z₃—A₄ | ﹇(CH₂)ₙ(CH₂)ₒ—Q |
|---|---|---|---|---|---|
| 155 | 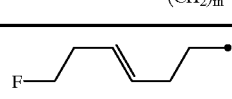 | | 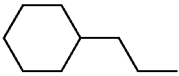 |  | 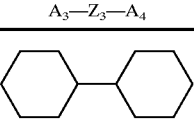 |
| 156 | 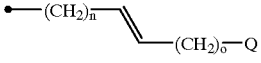 | | 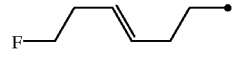 |  |  |
| 157 |  | | 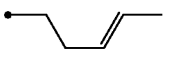 | 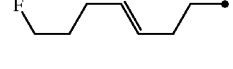 |  |
| 158 |  | |  |  | 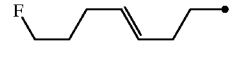 |
| 159 |  | |  |  |  |
| 160 | 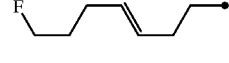 | |  |  |  |
TABLE 10
| | F—(CH₂)ₗ﹇(CH₂)ₘ﹈ | (A₁—Z₁)ₚ | (A₂—Z₂)_q | A₃—Z₃—A₄ | ﹇(CH₂)ₙ(CH₂)ₒ—Q |
|---|---|---|---|---|---|
| 161 | 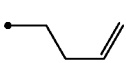 | 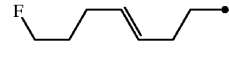 |  |  |  |
| 162 | 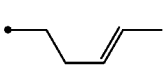 | 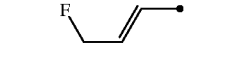 |  |  | 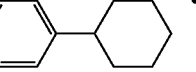 |
| 163 | 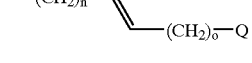 | 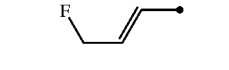 |  |  | 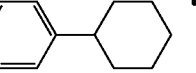 |
| 164 |  | 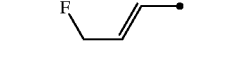 |  |  | 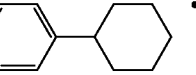 |
| 165 | 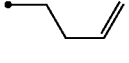 | 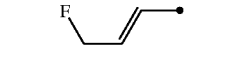 |  |  | 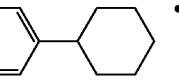 |
| 166 | 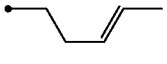 | 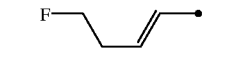 |  |  | 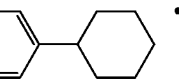 |

TABLE 10-continued

TABLE 11

TABLE 11-continued
| | F—(CH₂)ₗ⎯⎯(CH₂)ₘ—• | (A₁—Z₁)ₚ | (A₂—Z₂)q | A₃—Z₃—A₄ | •—(CH₂)ₙ⎯⎯(CH₂)ₒ—Q |
|---|---|---|---|---|---|
| 195 |  |  |  | 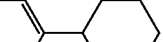 | 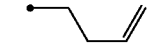 |
| 196 |  |  |  | 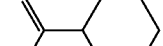 | 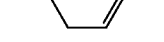 |
| 197 |  |  |  | 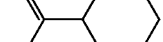 |  |
| 198 |  |  |  | 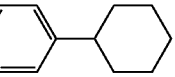 | 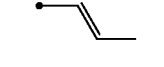 |
| 199 |  |  |  | 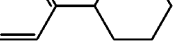 | 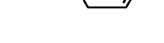 |
| 200 |  |  |  |  |  |
TABLE 12
| | F—(CH₂)ₗ⎯⎯(CH₂)ₘ—• | (A₁—Z₁)ₚ | (A₂—Z₂)q | A₃—Z₃—A₄ | •—(CH₂)ₙ⎯⎯(CH₂)ₒ—Q |
|---|---|---|---|---|---|
| 201 |  |  |  |  | 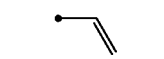 |
| 202 |  |  |  |  | 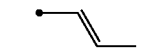 |
| 203 |  |  |  | 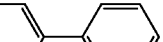 | 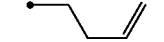 |
| 204 |  |  |  | 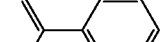 |  |
| 205 |  |  |  | 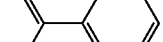 |  |
| 206 |  |  |  | 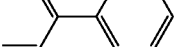 | 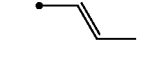 |

TABLE 12-continued
| | F—(CH₂)ₗ—(CH₂)ₘ—• | (A₁—Z₁)ₚ | (A₂—Z₂)q | A₃—Z₃—A₄ | •—(CH₂)ₙ—(CH₂)ₒ—Q |
|---|---|---|---|---|---|
| 207 | 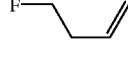 |  |  | 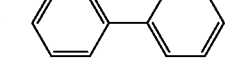 |  |
| 208 | 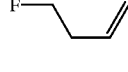 |  |  | 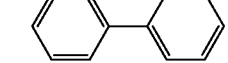 | 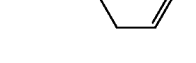 |
| 209 | 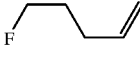 |  |  | 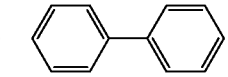 |  |
| 210 | 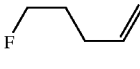 |  |  | 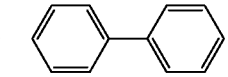 | 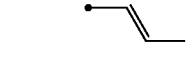 |
| 211 | 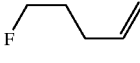 |  |  | 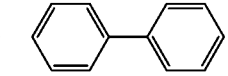 | 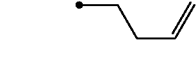 |
| 212 | 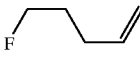 |  |  | 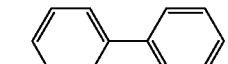 | 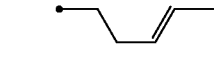 |
| 213 | 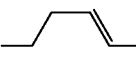 |  |  | 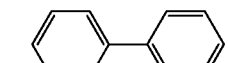 | 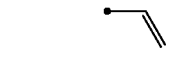 |
| 214 | 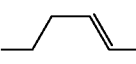 |  |  | 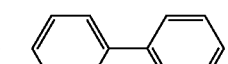 | 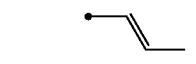 |
| 215 | 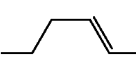 |  |  | 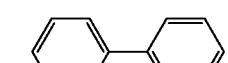 |  |
| 216 | 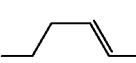 |  |  | 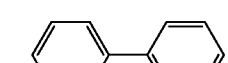 | 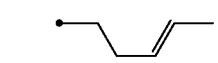 |
| 217 | 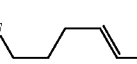 |  |  | 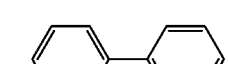 | 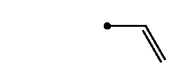 |
| 218 | 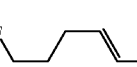 |  |  | 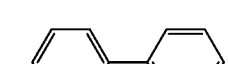 |  |
| 219 | 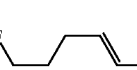 |  |  | 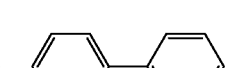 |  |
| 220 | 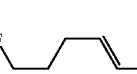 |  |  | 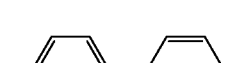 | 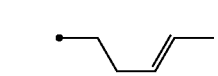 |

TABLE 13

| | $F-(CH_2)_l$ $(CH_2)_m$• | $(A_1-Z_1)_p$ | $(A_2-Z_2)_q$ | $A_3-Z_3-A_4$ | •$(CH_2)_n$ $(CH_2)_o-Q$ |
|---|---|---|---|---|---|
| 221 | | | | | |
| 222 | | | | | |
| 223 | | | | | |
| 224 | | | | | |
| 225 | | | | | |
| 226 | | | | | |
| 227 | | | | | |
| 228 | | | | | |
| 229 | | | | | |
| 230 | | | | | |
| 231 | | | | | |
| 232 | | | | | |
| 233 | | | | | |
| 234 | | | | | |

TABLE 13-continued
| | F—(CH₂)ₗ—〰—(CH₂)ₘ—• | (A₁—Z₁)ₚ | (A₂—Z₂)_q | A₃—Z₃—A₄ | •—(CH₂)ₙ—〰—(CH₂)ₒ—Q |
|---|---|---|---|---|---|
| 235 | 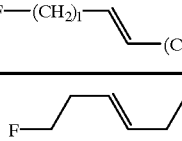 |  |  |  |  |
| 236 | 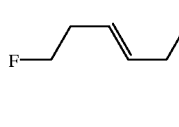 |  |  | 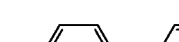 |  |
| 237 | 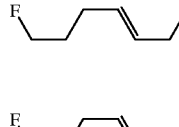 |  |  | 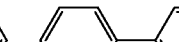 |  |
| 238 | 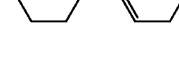 |  |  |  |  |
| 239 | 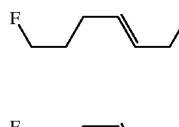 |  |  | 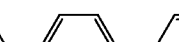 | 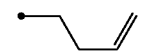 |
| 240 | 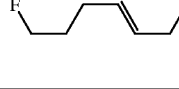 |  |  |  | 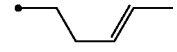 |
TABLE 14
| | F—(CH₂)ₗ—〰—(CH₂)ₘ—• | (A₁—Z₁)ₚ | (A₂—Z₂)_q | A₃—Z₃—A₄ | •—(CH₂)ₙ—〰—(CH₂)ₒ—Q |
|---|---|---|---|---|---|
| 241 | 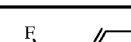 | | | 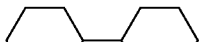 | 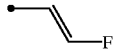 |
| 242 | 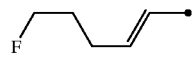 | | | 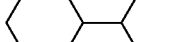 | 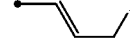 |
| 243 |  | | | 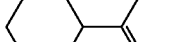 | 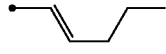 |
| 244 | 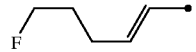 | | | 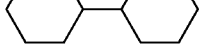 | 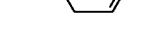 |
| 245 |  | | | 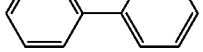 | 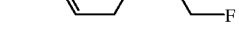 |
| 246 |  | | |  | 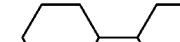 |

TABLE 14-continued

| $F-(CH_2)_l \diagup \diagdown (CH_2)_m-\bullet$ | $(A_1-Z_1)_p$ | $(A_2-Z_2)_q$ | $A_3-Z_3-A_4$ | $\bullet-(CH_2)_n \diagup \diagdown (CH_2)_o-Q$ |
|---|---|---|---|---|
| 247 | | Cy | Cy-Cy | |
| 248 | | Cy | Cy-Ph | |
| 249 | | Ph | Cy-Cy | |
| 250 | | Cy | Ph-Cy | |
| 251 | | Cy | Ph-Cy | |
| 252 | | Cy | Ph-Ph | |
| 253 | Cy | Cy | Cy-Cy | |
| 254 | Cy | Cy | Cy-Cy | |
| 255 | Cy-CH$_2$CH$_2$ | Cy | Ph-Ph | |
| 256 | Ph | Cy | Ph-Cy | |
| 257 | Cy | Cy | Ph-Ph | |

TABLE 14-continued

| No. | F—(CH$_2$)$_l$—/=\—(CH$_2$)$_m$—• | (A$_1$—Z$_1$)$_p$ | (A$_2$—Z$_2$)$_q$ | A$_3$—Z$_3$—A$_4$ | •—(CH$_2$)$_n$—/=\—(CH$_2$)$_o$—Q |
|---|---|---|---|---|---|
| 258 | F\\=/• | ⬡ | ⬡ | ⬡—⬡ | •\\=/—F |
| 259 | F—\\=/• | ⬡ | ⬡ | ⬡—⬡ | •\\=/\\—F |
| 260 | F\\/=\\/• | ⬡ | ⬡ | ⬡—⬡ | •\\/=\\—F |
| 261 | F—\\=/\\• | ⬡ | ⬡ | ⬡—⬡ | •\\=/\\—F |
| 262 | F—/=\\/• | ⬡ | ⬡ | ⬡—⬡ | •\\=/—F |

EXAMPLE 4

(Use Example 1)

Liquid crystal composition (mother liquid crystal) comprising

| | |
|---|---|
| 4-(trans-4-propylcyclohexyl)benzonitrile | 30% by weight |
| 4-(trans-4-pentylcyclohexyl)benzonitrile | 40% by weight |
| 4-(trans-4-heptylcyclohexyl)benzonitrile | 30% by weight | was prepared. This composition had a clearing point (Cp.) of 52.3° C., Δε of 10.7, Δn of 0.119, viscosity at 20° C. ($\eta_{20}$) of 21.4 mPa·s, and Vth when filled in a TN cell of 9 μm thickness of 1.60 V.

When a liquid crystal composition was prepared by mixing 15 parts by weight of the compound of the present invention, 1-(3-butenyl)-trans-4-(trans-4-((E)-(5-fluoro-1-pentenyl)cyclohexyl) cyclohexane (Compound No. 11), obtained in Example 1 with 85 parts by weight of the mother liquid crystal described above, the composition thus obtained had a Cp. of 54.2° C., $V_{th}$ of 1.61 V, Δε of 9.3, Δn of 0.109, $\eta_{20}$ of 19.0 mPa·s, $K_{33}/K_{11}$ of 2.23, and Vth when filled in a TN cell of 9 μm thickness of 1.61 V. Whereas this liquid crystal composition was left in a freezer at −20° C. for 25 days, separation of crystals and development of a smectic phase were not observed.

Comparative Example

For comparison, a compound expressed by the formula (a) recited above wherein R represents propyl group and alkenyl is 3-butenyl group was synthesized, a liquid crystal composition was prepared in the same manner as in Example 4 with the exception that the comparative compound was used in place of the compound (Compound No. 11), and then $K_{33}/K_{11}$ of the liquid crystal composition thus obtained was determined to find to be 1.78.

This value was clearly poor compared with that of 2.23 obtained when the compound mentioned above (Compound No. 11) was used (as shown in Example 4).

INDUSTRIAL APPLICABILITY

As described above, any compounds of the present invention are considerably excellent as liquid crystal compound particularly for STN display mode, since they have a wide temperature range of a liquid crystal phase, low viscosity, medium degree of Δε, and large $K_{33}/K_{11}$, and they are readily mixed with various other liquid crystal materials even at low temperatures.

Accordingly, when the compounds of the present invention are used as component of liquid crystal compositions, novel liquid crystal compositions which have desired physical properties in addition to a characteristic of having an excellent mutual solubility with other liquid crystal materials, can be provided by suitably selecting six-membered rings, substituents and/or bonding groups of molecule constituting elements.

We claim:

1. A fluoroalkenyl derivative expressed by the general formula (1)

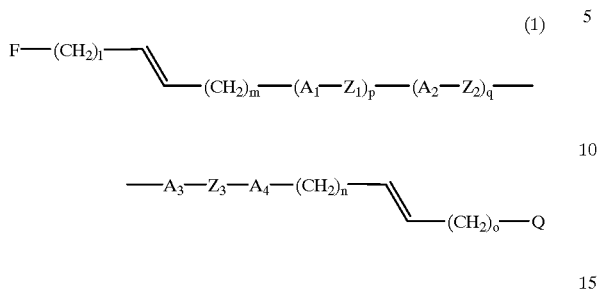

wherein $A_1$, $A_2$, $A_3$, and $A_4$ independently represent trans-1,4-cyclohexylene group or 1,4-phenylene group at least one hydrogen atom on which six-membered ring may be replaced by a halogen atom; $Z_1$, $Z_2$, and $Z_3$ independently represent —(CH$_2$)$_2$—, —CH=CH—, —C≡C—, or a single bond; Q represents H or F; l is an integer of 1 to 5; m, n, and o are independently an integer of 0 to 5; p and q are independently an integer of 0 or 1.

2. The fluoroalkenyl derivative according to claim 1 wherein $Z_3$ represents a single bond; both $A_3$ and $A_4$ represent trans-1,4-cyclohexylene group; and both p and q are 0.

3. The fluoroalkenyl derivative according to claim 1 wherein both $Z_2$ and $Z_3$ represent a single bond; $A_2$, $A_3$, and $A_4$ represent trans-1,4-cyclohexylene group; p is 0; and q is 1.

4. The fluoroalkenyl derivative according to claim 1 wherein both $Z_2$ and $Z_3$ represent a single bond; both $A_2$ and $A_4$ represent trans-1,4-cyclohexylene group; $A_3$ represents 1,4-phenylene group; p is 0; and q is 1.

5. The fluoroalkenyl derivative according to claim 1 wherein $Z_1$, $Z_2$, and $Z_3$ represent a single bond; both $A_1$ and $A_4$ represent trans-1,4-cyclohexylene group; both $A_2$ and $A_3$ represent 1,4-phenylene group; and both p and q are 1.

6. A liquid crystal composition comprising at least 2 components and comprising at least one fluoroalkenyl derivative defined in any one of claims 1 to 5.

7. A liquid crystal composition comprising, as a first component, at least one fluoroalkenyl derivative defined in any one of claims 1 to 5, and comprising, as a second component, at least one compound selected from the group consisting of the compounds expressed by any one of the general formulas (2), (3), and (4)

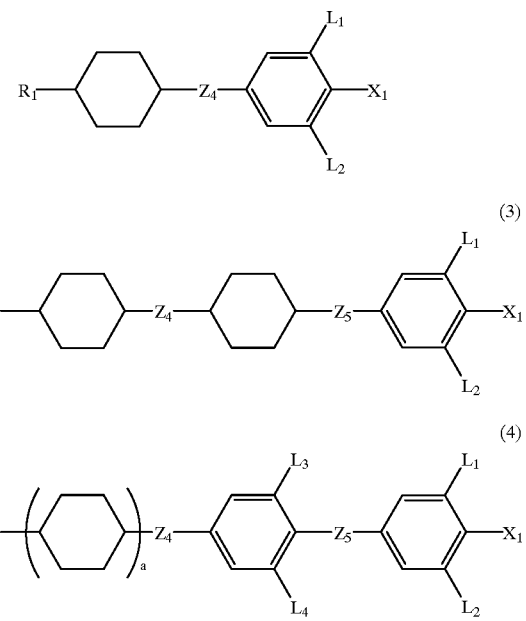

wherein $R_1$ represents an alkyl group having 1 to 10 carbon atoms; $X_1$ represents F, Cl, OCF$_3$, OCF$_2$H, CF$_3$, CF$_2$H, or CFH$_2$; $L_1$, $L_2$, $L_3$, and $L_4$ independently represent H or F; $Z_4$ and $Z_5$ independently represent —(CH$_2$)$_2$—, —CH=CH—, or a covalent bond; and a is 1 or 2.

8. A liquid crystal display device comprising a liquid crystal composition defined in claim 6.

9. A liquid crystal display device comprising a liquid crystal composition defined in claim 7.

10. A liquid crystal composition comprising, as a first component, at least one fluoroalkenyl derivative defined in any one of claims 1 to 5, and as a second component, at least one compound selected from the group consisting of the compounds expressed by any one of the general formulas (5), (6), (7), (8) and (9)

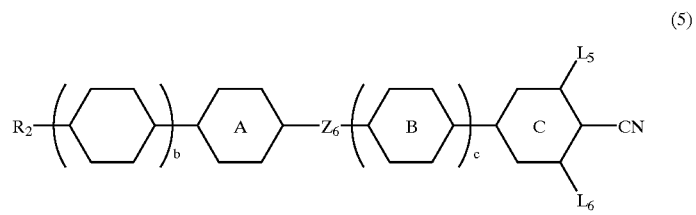

wherein $R_2$ represents F, an alkyl group having 1 to 10 carbon atoms, or an alkenyl group having 2 to 10 carbon atoms, in which alkyl group or alkenyl group one or more non-adjacent methylene groups (—CH$_2$—) may each be replaced by an oxygen atom (—O—); ring A represents trans-1,4-cyclohexylene group, 1,4-phenylene group, pyrimidine-2,5-diyl group, or 1,3-dioxane-2,5-diyl group; ring B represents trans-1,4-cyclohexylene group, 1,4-phenylene group, or pyrimidine-2,5-diyl group; ring C represents trans-1,4-cyclohexylene group or 1,4-phenylene group; $Z_6$ represents —(CH$_2$)$_2$—, —COO—, or a single bond; $L_5$ and $L_6$ independently represent H or F; and b and c are independently 0 or 1, (6)

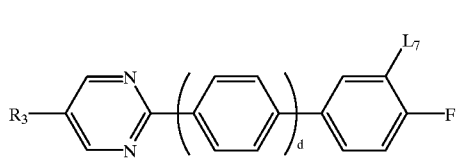

wherein $R_3$ represents an alkyl group having 1 to 10 carbon atoms; $L_7$ represents H or F; and d is 0 or 1, (7)

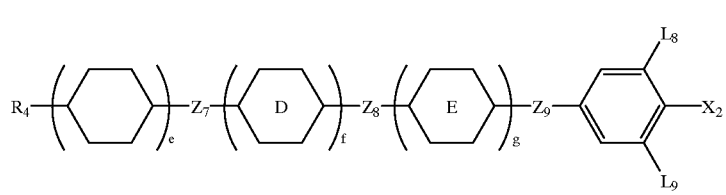

wherein $R_4$ represents an alkyl group having 1 to 10 carbon atoms; ring D and ring E independently represent trans-1, 4-cyclohexylene group or 1,4-phenylene group; $Z_7$ and $Z_8$ independently represent —COO— or a single bond; $Z_9$ represents —COO— or —C≡C—; $L_8$ and $L_9$ independently represent H or F; $X_2$ represents F, OCF$_3$, OCF$_2$H, CF$_3$, CF$_2$H, or CFH$_2$; and e, f, and g are independently 0 or 1, (8)

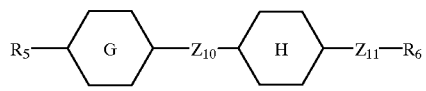

wherein $R_5$ and $R_6$ independently represent an alkyl group having 1 to 10 carbon atoms or an alkenyl group having 2 to 10 carbon atoms, in which alkyl or alkenyl group one or more non-adjacent methylene groups (—CH$_2$—) may each be replaced by an oxygen atom (—O—); ring G represents trans-1, 4-cyclohexylene group, 1, 4-phenylene group, or pyrimidine-2,5-diyl group; ring H represents trans-1,4-cyclohexylene group or 1,4-phenylene group; $Z_{10}$ represents —C≡C—, —COO—, —(CH$_2$)$_2$—, —CH=CH—C≡C—, or a single bond; and $Z_{11}$ represents —COO— or a single bond, wherein $R_7$ and $R_8$ independently represent an alkyl group having 1 to 10 carbon atoms or an alkenyl group having 2 to 10 carbon atoms, in which alkyl or alkenyl group one or more non-adjacent methylene groups (—CH$_2$—) may each be replaced by an oxygen atom (—O—); ring I represents trans-1,4-cyclohexylene group, 1,4-phenylene group, or pyrimidine-2,5-diyl group; ring J represents trans-1,4-cyclohexylene group, 1,4-phenylene group at least one hydrogen atom on which ring may be replaced by F, or pyrimidine-2,5-diyl group; ring K represents trans-1,4-cyclohexylene group or 1,4-phenylene group; $Z_{12}$ and $Z_{14}$ independently represent —COO—, —(CH$_2$)$_2$—, or a single bond; $Z_{13}$ represents —CH=CH—, —C≡C—, —COO—, or a single bond; and h is 0 or 1.

11. A liquid crystal composition comprising, as a first component, at least one fluoroalkenyl derivative defined in any one of claims 1 to 5, as a part of a second component, at least one compound selected from the group consisting of the compounds expressed by any one of the general formulas (2), (3) and (4), and as another part of the second component, at least one compound selected from the group consisting of the compounds expressed by any one of the general formulas (5), (6), (7), (8) and (9), (2)

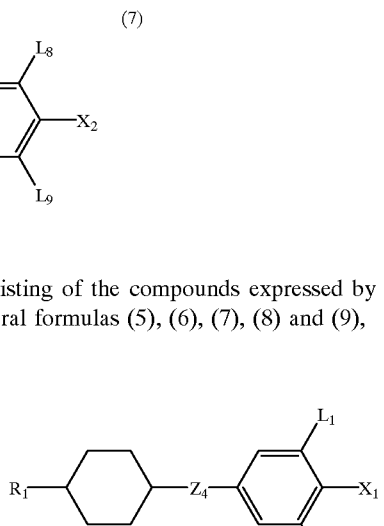

(3)

consisting of the compounds expressed by any one of the general formulas (5), (6), (7), (8) and (9), (9)

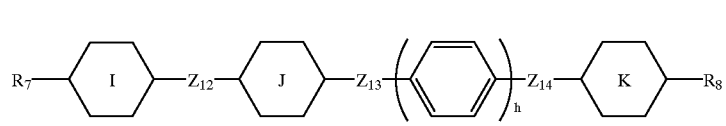

(4)

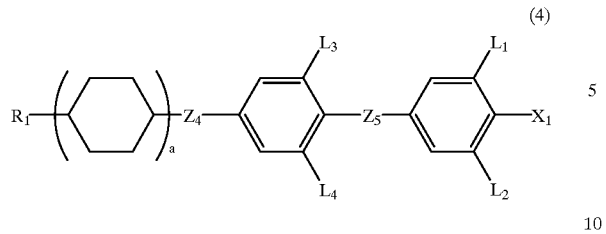

wherein $R_1$ represents an alkyl group having 1 to 10 carbon atoms; $X_1$ represents F, Cl, $OCF_3$, $OCF_2H$, $CF_3$, $CF_2H$, or $CFH_2$; $L_1$, $L_2$, $L_3$, and $L_4$ independently represent H or F; $Z_4$ and $Z_5$ independently represent $—(CH_2)_2—$, $—CH=CH—$, or a single bond; and a is 1 or 2, (5)

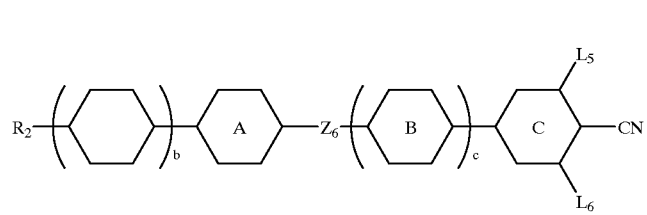

wherein $R_2$ represents F, an alkyl group having 1 to 10 carbon atoms, or an alkenyl group having 2 to 10 carbon atoms, in which alkyl group or alkenyl group one or more non-adjacent methylene groups ($—CH_2—$) may each be replaced by an oxygen atom ($—O—$); ring A represents trans-1,4-cyclohexylene group, 1,4-phenylene group, pyrimidine-2,5-diyl group, or 1,3-dioxane-2,5-diyl group; ring B represents trans-1,4-cyclohexylene group, 1,4-phenylene group, or pyrimidine-2,5-diyl group; ring C represents trans-1,4-cyclohexylene group or 1, 4-phenylene group; $Z_6$ represents $—(CH_2)_2—$, $—COO—$, or a single bond; $L_5$ and $L_6$ independently represent H or F; and b and c are independently 0 or 1, (6)

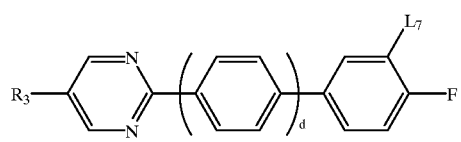

wherein $R_3$ represents an alkyl group having 1 to 10 carbon atoms; $L_7$ represents H or F; and d is 0 or 1, wherein $R_4$ represents an alkyl group having 1 to 10 carbon atoms; ring D and ring E independently represent trans-1, 4-cyclohexylene group or 1,4-phenylene group; $Z_7$ and $Z$, independently represent $—COO—$ or a single bond; $Z_9$ represents $—COO—$ or $—C≡C—$; $L_8$ and $L_9$ independently represent H or F; $X_2$ represents F, $OCF_3$, $OCF_2H$, $CF_3$, $CF_2H$, or $CFH_2$; and e, f, and g are independently 0 or 1, (8)

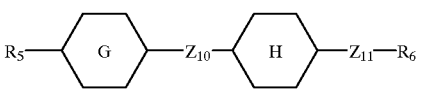

wherein $R_5$ and $R_6$ independently represent an alkyl group having 1 to 10 carbon atoms or an alkenyl group having 2 to 10 carbon atoms, in which alkyl or alkenyl group one or more non-adjacent methylene groups ($—CH_2—$) may each be replaced by an oxygen atom ($—O—$); ring G represents trans-1,4-cyclohexylene group, 1,4-phenylene group, or pyrimidine-2,5-diyl group; ring H represents trans-1,4-cyclohexylene group or 1,4-phenylene group; $Z_{10}$ represents $—C≡C—$, $—COO—$, $—(CH_2)_2—$, $—CH=CH—C≡C—$, or a single bond; and $Z_{11}$ represents $—COO—$ or a single bond, and $Z_{11}$ represents $—COO—$ or a single bond, (7)

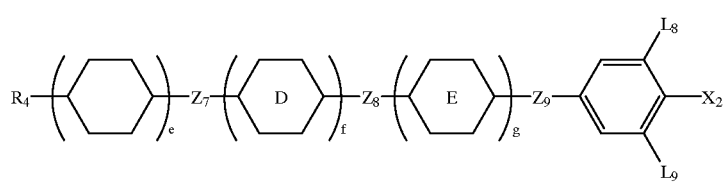

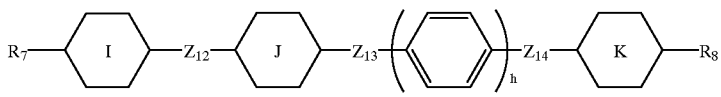

(9)

wherein $R_7$ and $R_8$ independently represent an alkyl group having 1 to 10 carbon atoms or an alkenyl group having 2 to 10 carbon atoms, in which alkyl or alkenyl group one or more non-adjacent methylene groups (—$CH_2$—) may each be replaced by an oxygen atom (—O—); ring I represents trans-1,4-cyclohexylene group, 1,4-phenylene group, or pyrimidine-2,5-diyl group; ring J represents trans-1,4-cyclohexylene group, 1,4-phenylene group at least one hydrogen atom on which ring may be replaced by F, or pyrimidine-2,5-diyl group; ring K represents trans-1,4-cyclohexylene group or 1,4-phenylene group; $Z_{12}$ and $Z_{14}$ independently represent —COO—, —$(CH_2)_2$—, or a single bond; $Z_{13}$ represents —CH=CH—, —C≡C—, —COO—, or a single bond; and h is 0 or 1.

12. A liquid crystal display device comprising a liquid crystal composition defined in claim 10.

13. A liquid crystal display device comprising a liquid crystal composition defined in claim 11.

* * * * *